(12) United States Patent
Murao et al.

(10) Patent No.: US 12,318,400 B2
(45) Date of Patent: Jun. 3, 2025

(54) BROWN AND BEIGE ADIPOCYTE ACTIVATING AGENT CONTAINING D-ALLULOSE AS ACTIVE INGREDIENT

(71) Applicant: NATIONAL UNIVERSITY CORPORATION KAGAWA UNIVERSITY, Takamatsu (JP)

(72) Inventors: Koji Murao, Takamatsu (JP); Hitomi Imachi, Takamatsu (JP); Ken Izumori, Takamatsu (JP); Akihide Yoshihara, Takamatsu (JP)

(73) Assignee: NATIONAL UNIVERSITY CORPORATION KAGAWA UNIVERSITY, Takamatsu (JP)

( * ) Notice: Subject to any disclaimer, the term of this patent is extended or adjusted under 35 U.S.C. 154(b) by 1018 days.

(21) Appl. No.: 17/292,166

(22) PCT Filed: Nov. 7, 2019

(86) PCT No.: PCT/JP2019/043703
§ 371 (c)(1),
(2) Date: May 7, 2021

(87) PCT Pub. No.: WO2020/096002
PCT Pub. Date: May 14, 2020

(65) Prior Publication Data
US 2021/0386767 A1 Dec. 16, 2021

(30) Foreign Application Priority Data
Nov. 8, 2018 (JP) .................. 2018-210262

(51) Int. Cl.
| | |
|---|---|
| A61K 31/7004 | (2006.01) |
| A23K 20/163 | (2016.01) |
| A23L 2/52 | (2006.01) |
| A23L 33/00 | (2016.01) |
| A23L 33/125 | (2016.01) |
| A61P 3/04 | (2006.01) |
| A61P 3/10 | (2006.01) |

(52) U.S. Cl.
CPC ........ *A61K 31/7004* (2013.01); *A23K 20/163* (2016.05); *A23L 2/52* (2013.01); *A23L 33/125* (2016.08); *A23L 33/40* (2016.08); *A61P 3/04* (2018.01); *A61P 3/10* (2018.01); *A23V 2002/00* (2013.01)

(58) Field of Classification Search
None
See application file for complete search history.

(56) References Cited

U.S. PATENT DOCUMENTS

| | | |
|---|---|---|
| 9,109,266 B2 | 8/2015 | Takamine et al. |
| 2016/0151305 A1 | 6/2016 | Takako et al. |
| 2018/0243325 A1 | 8/2018 | Choi et al. |

FOREIGN PATENT DOCUMENTS

| | | |
|---|---|---|
| EP | 3345608 A1 | 7/2018 |
| WO | 2010/113785 A1 | 10/2010 |
| WO | 2014/175119 A1 | 10/2014 |

OTHER PUBLICATIONS

Iwasaki et al., Nature Communications, 1.9.18, vol. 9, No. 1, pp. 1-17. (Year: 2018).*
Iwasaki et al., Nature Communications, 1.9.18, vol. 9, No. 1, pp. 1-17.*
Iwasaki, Yusaku: "GLP-1 release and vagal afferent activation mediate the beneficial metabolic and chronotherapeutic effects of D-allulose—Supplementary figures", Nature Communications, Jan. 9, 2018, pp. 1-9; Cited in Supplementary European Search Report dated Jun. 15, 2022.
Min-Yu Chung et al: "Hypoglycemic Health Benefits of D-Psicose", Journal of Agricultural and Food Chemistry, vol. 60, No. 4, Feb. 1, 2012, pp. 863-869; Cited in Supplementary European Search Report dated Jun. 15, 2022. (7 pages).
Young-Mee Chung et al: "Dietary D-Psicose Reduced Visceral Fat Mass in High-Fat Diet-Induced Obese Rats", Journal of Food Science, vol. 77, No. 2, Feb. 1, 2012, pp. H53-H58; Cited in Supplementary European Search Report dated Jun. 15, 2022. (6 pages).
Do Ga Young et al: "Supplementation of Non-Dairy Creamer-Enriched High-Fat Diet with D-Allulose Ameliorated Blood Glucose and Body Fat Accumulation in C57BL/6J Mice", Applied Sciences, vol. 9, No. 13, Jul. 8, 2019, p. 2750; Cited in Supplementary European Search Report dated Jun. 15, 2022. (17 pages).
Supplementary European Search Report dated Jun. 15, 2022, issued in counterpart EP Application No. 19881272.9. (4 pages).
Takamine et al., "Manufacturing Method of Rare Sugar Syrup through Alkali Isomerization and its Inhibitory Effect of a-Glucosidase", Bulletin of Applied Glycoscience, 2015, vol. 1, No. 1, pp. 44-49, with English translation, (5 pages).
Shimomura et al., "Role of obesity-abnormal production of adipocytokines", The Journal of the Japanese Society of Internal Medicine, 2004, vol. 93, No. 4, pp. 655-666, with English abstract, (8 pages).
Ikeda et al., "The common and distinct features of brown and beige adipocytes", Trends Endocrinol Metab., 2018, vol. 29, No. 3, pp. 191-200, (14 pages).

(Continued)

*Primary Examiner* — Traviss C McIntosh, III
(74) *Attorney, Agent, or Firm* — WHDA, LLP

(57) ABSTRACT

To provide a brown and beige adipocyte activating agent and a brown and beige adipocyte activating food, each containing D-allulose as an active ingredient. Provided are a brown and beige adipocyte activating agent containing D-allulose as an active ingredient; a brown and beige adipocyte activating agent containing at least D-allulose and having a UCP-1 expression promoting action; a brown and beige adipocyte activating agent which enhances UCP-1 expression and thereby activates brown and beige adipocytes; an energy consumption promoting agent containing D-allulose as an active ingredient; an energy consumption promoting agent which activates brown and beige adipocytes and thereby promotes energy consumption; a UCP-1 expression enhancing agent containing D-allulose as an active ingredient; and a composition or food composition containing these agents.

7 Claims, 15 Drawing Sheets

(56) References Cited

OTHER PUBLICATIONS

Iwasaki et al., "GLP-1 release and vagal afferent activation mediate the beneficial metabolic and chronotherapeutic effects of D-allulose", Nature Communications, 2018, vol. 9, No. 1, Article No. 113, pp. 1-17, cited in ISR dated Dec. 17, 2019. (17 pages).
Imachi et al., "Rare sugar D-psicose reduces TNF-a and MCP-1 in patients with type 2 diabetic patients", Journal of the Japan Diabetic Society, 2013, vol. 56, suppl., p. S231, with partial translation, cited in ISR dated Dec. 17, 2019. (2 pages).
International Search Report dated Dec. 17, 2019, issued in counterpart application No. PCT/JP2019/043703. (2 pages).
Office Action dated Aug. 27, 2024, issued in counterpart EP application No. 19881272.9. (12 pages).
Giacobino, J-P et al., "Thermogenic brown adipocytes as new targets for the treatment of obesity in humans", Clinical Lipidology, Future Medicine Ltd, GB, Jan. 1, 2010 (Jan. 1, 2010) vol. 5, No. 2, pp. 173-180. (8 pages).

* cited by examiner

[Fig. 1]
The effect of D-allulose on body weight and blood glucose
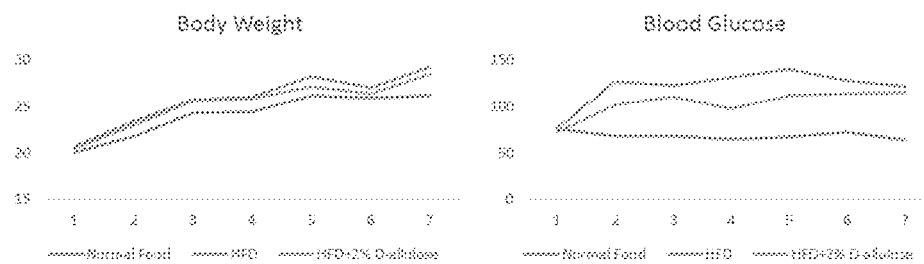
[Fig. 2]
The effect of D-allulose on BAT weight
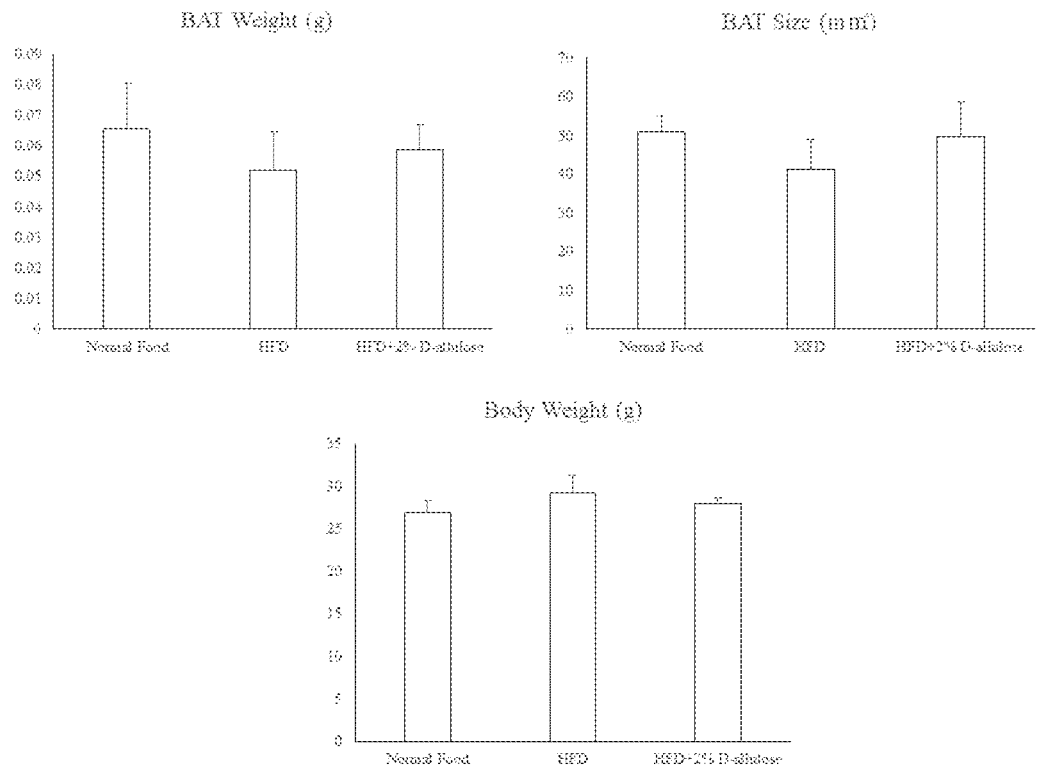

[Fig. 3]
D-allulose improved HFD induced hepatic steatosis
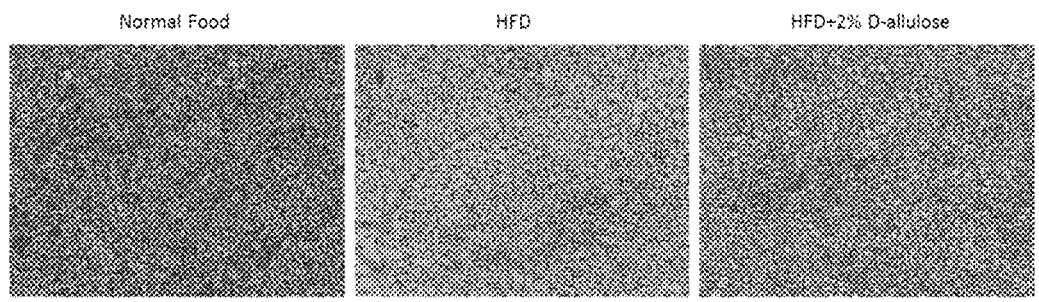
[Fig. 4]
The effect of D-allulose on BAT gene expression
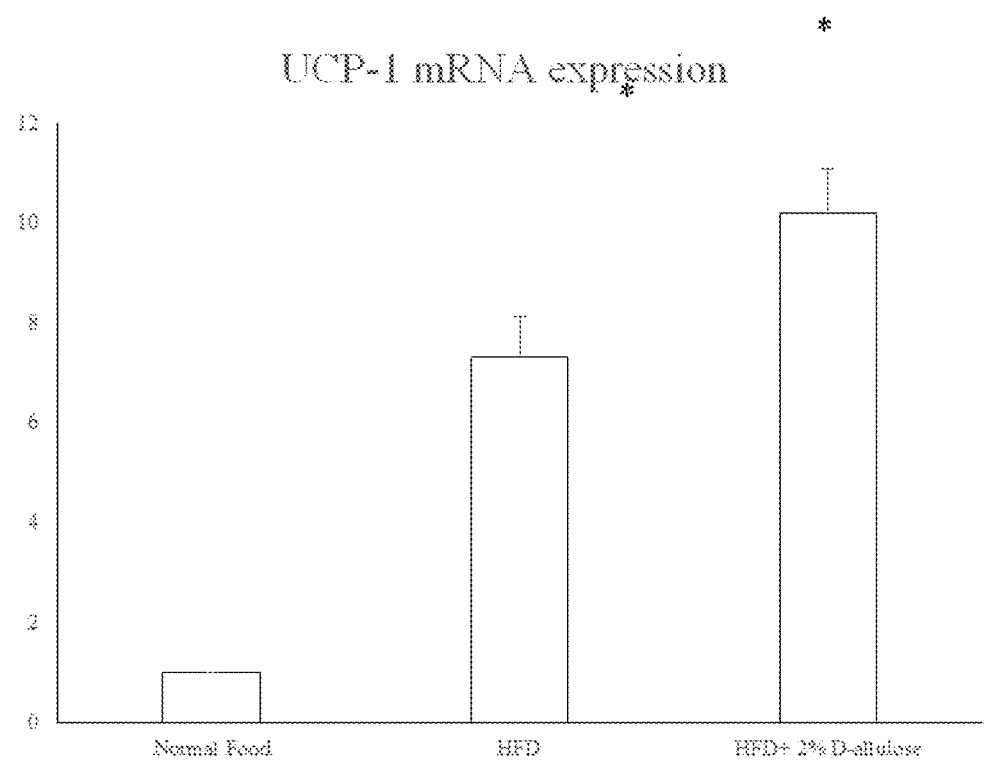

[Fig. 5]
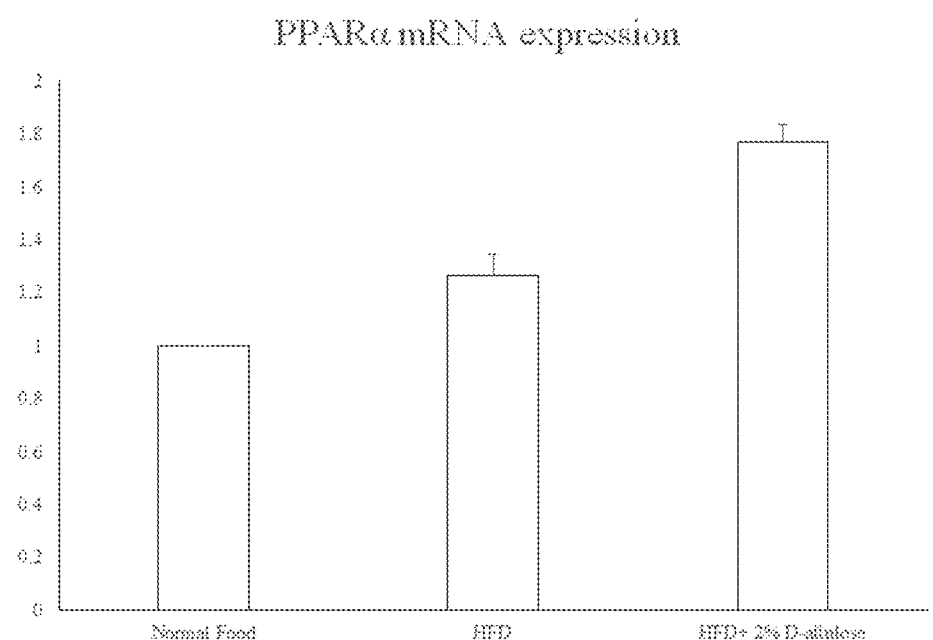

[Fig. 6]
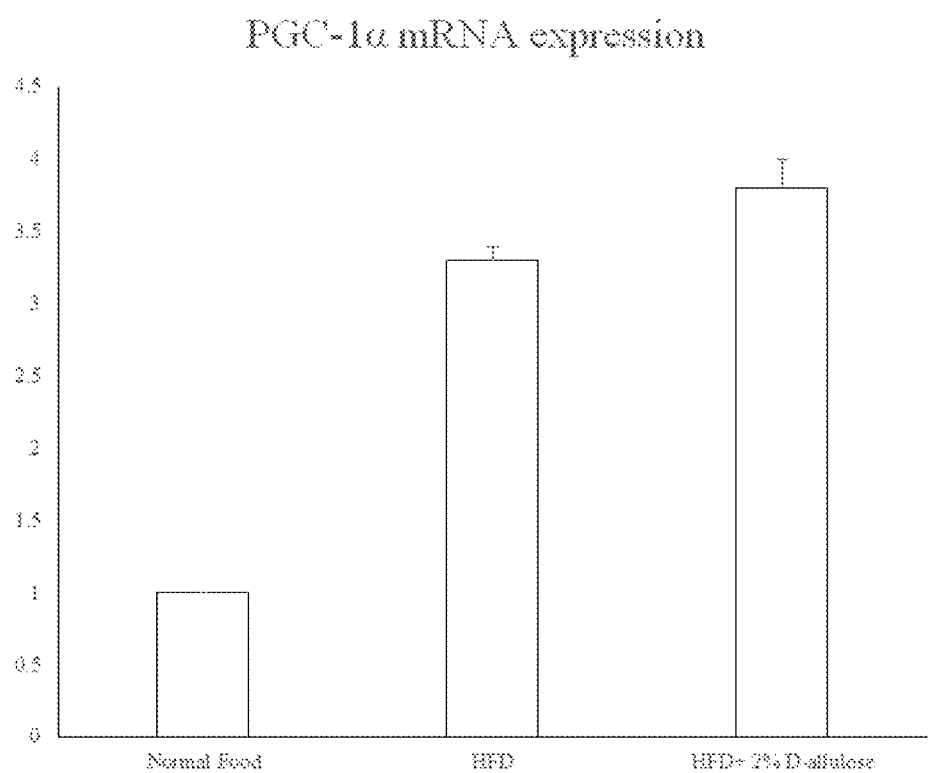
[Fig. 7]
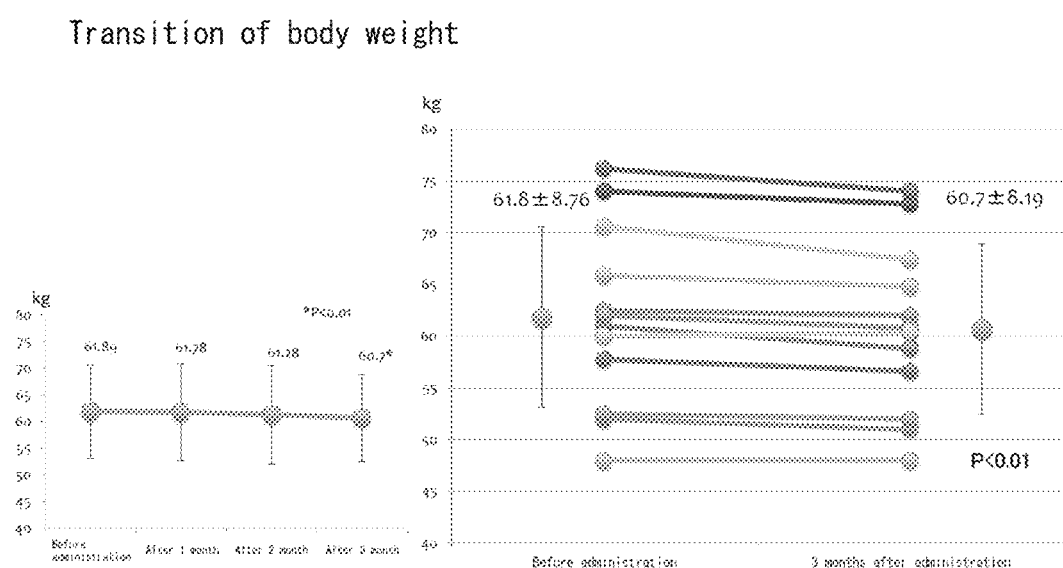

[Fig. 8]
Various adipose tissue-derived physiologically active substances (Adipocytokine) and action thereof
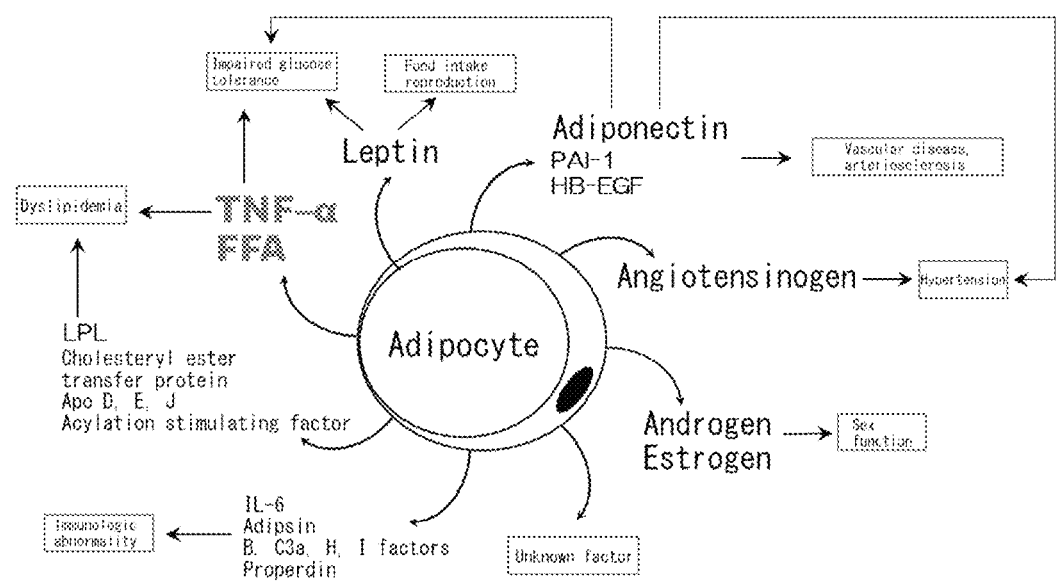

[Fig. 9]
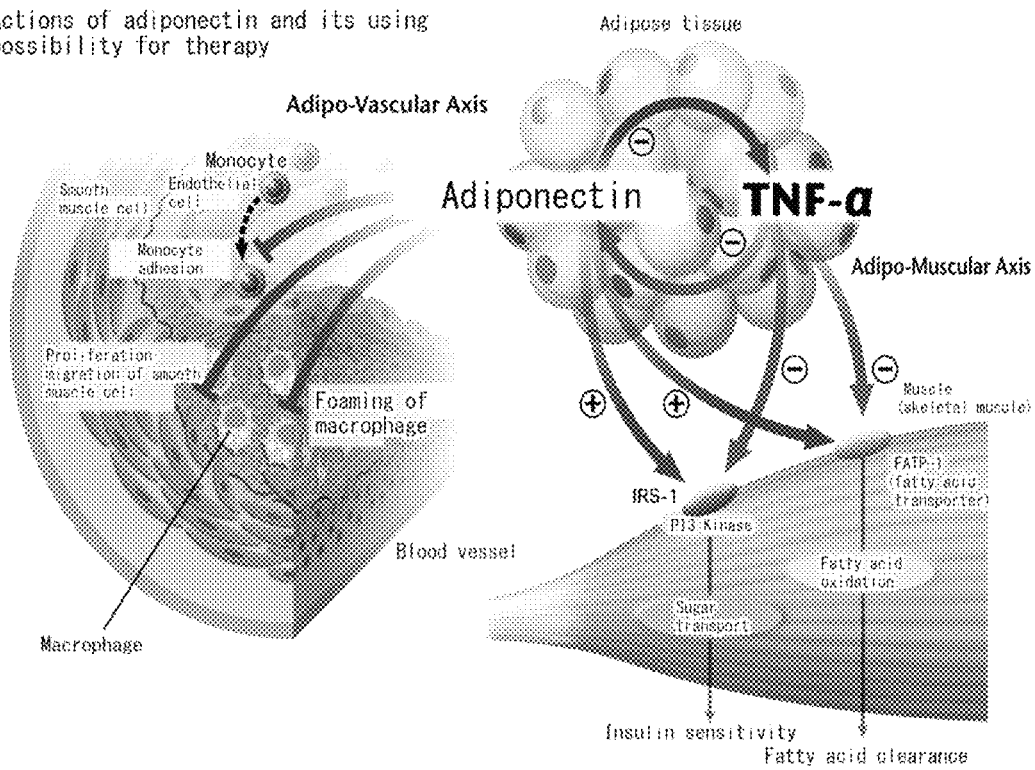
[Fig. 10]
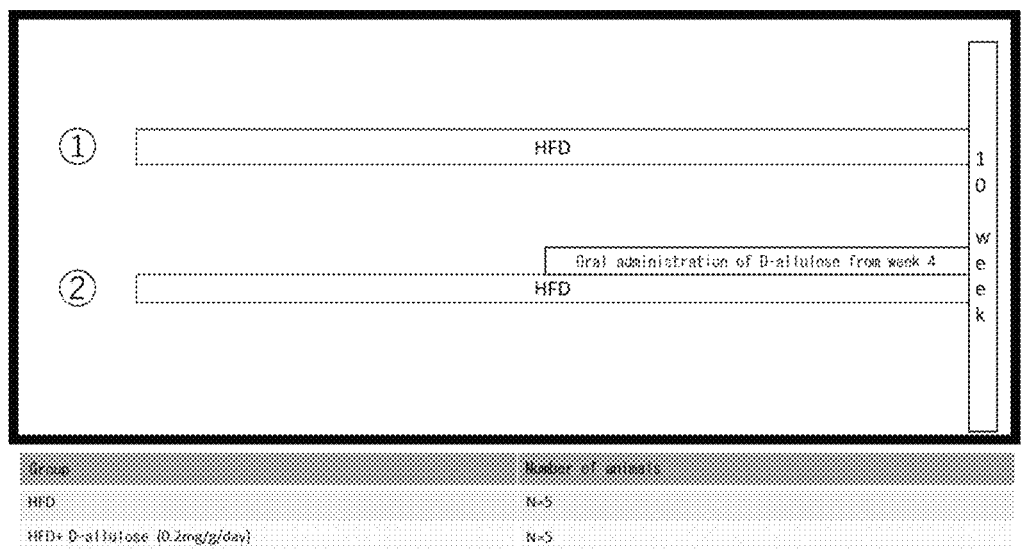

[Fig. 11]
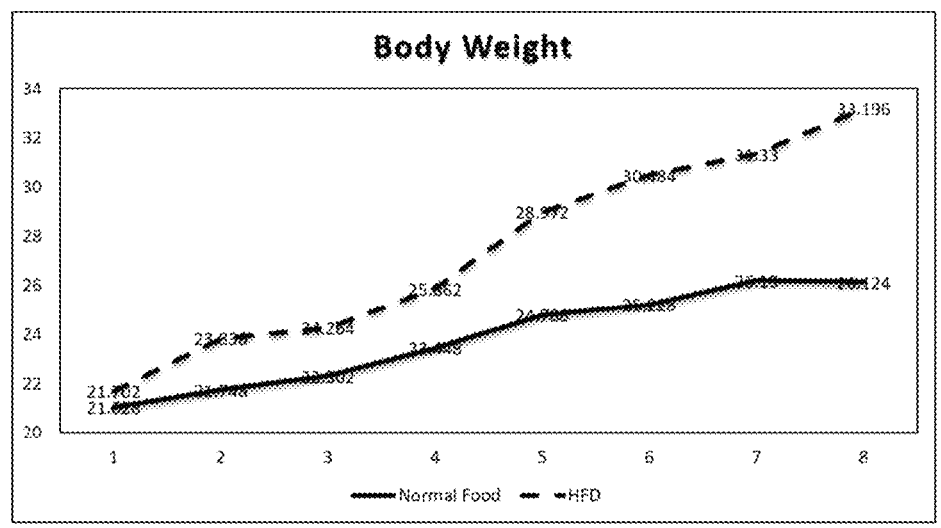
[Fig. 12]
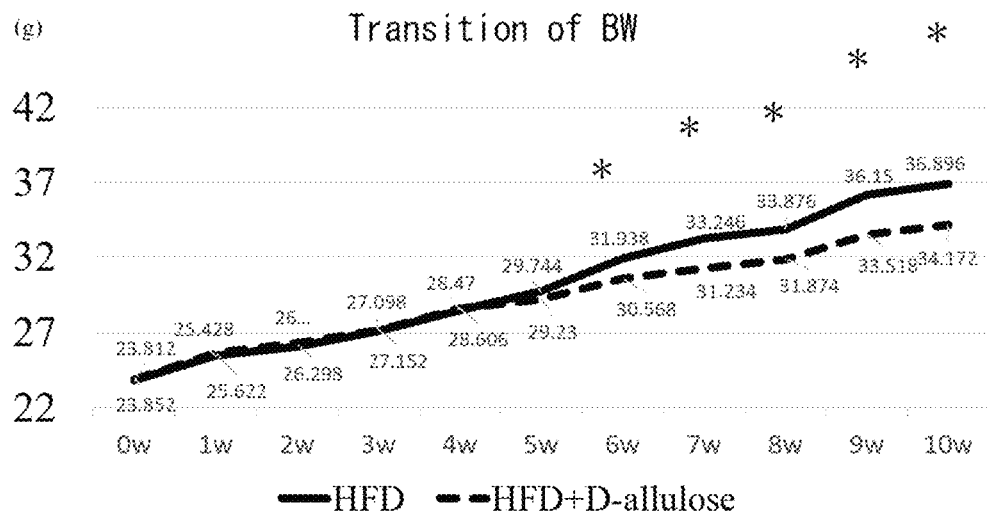

[Fig. 13]
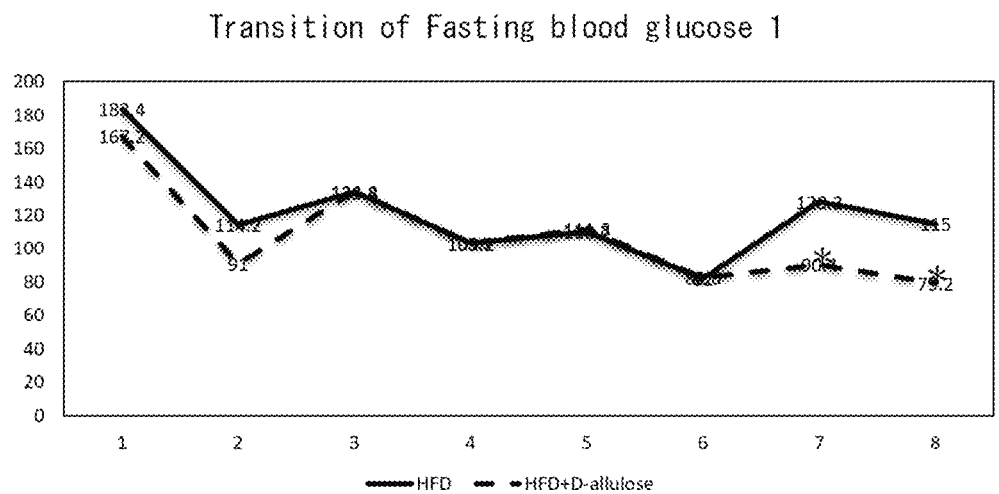
[Fig. 14]
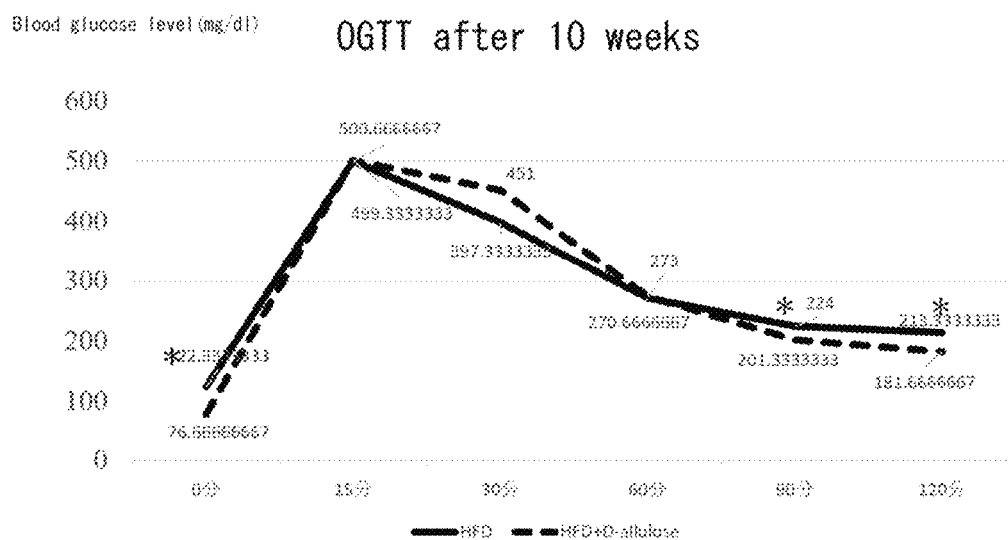

[Fig. 15]
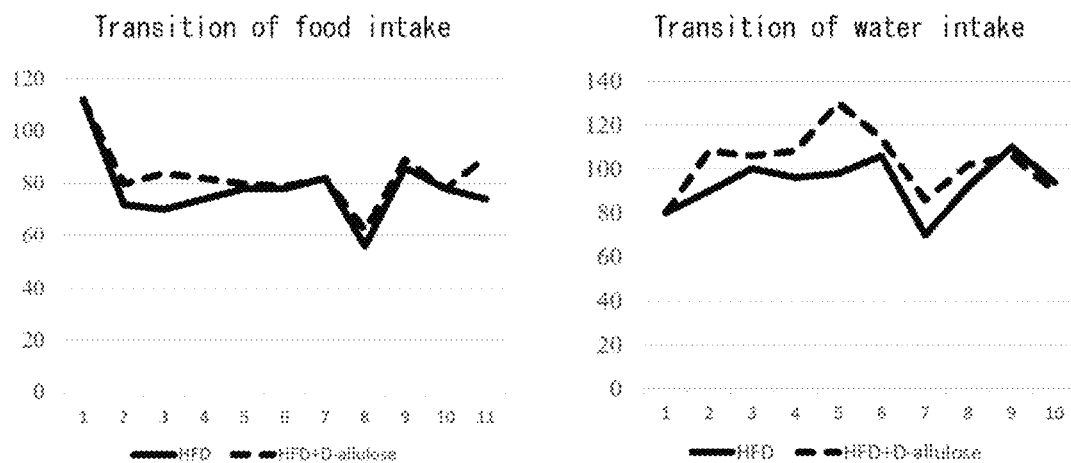
[Fig. 16]
Weight and area of brown adipose tissue
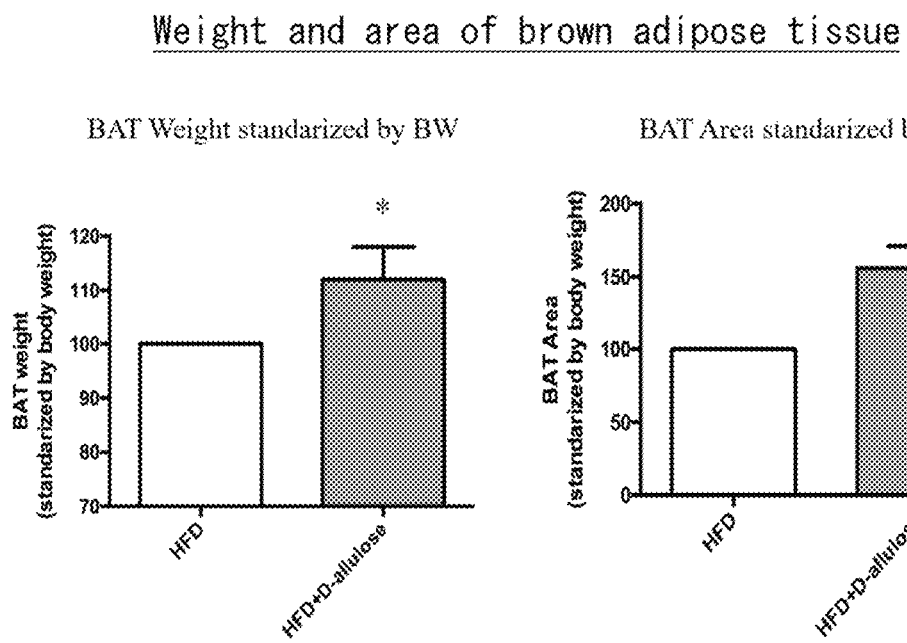

[Fig. 17]
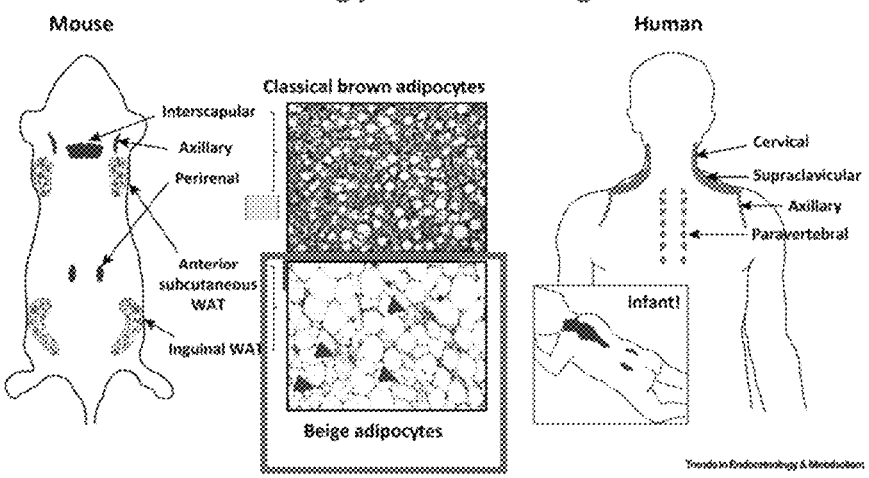
Ikeda K, etc. : TEM 2018;29:191-200.
[Fig. 18]
UCP1 mRNA level
Beige Adipose Tissue
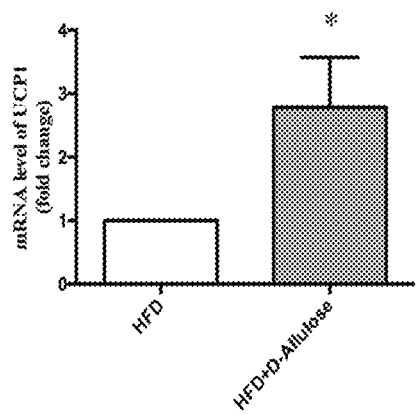
Brown Adipose Tissue
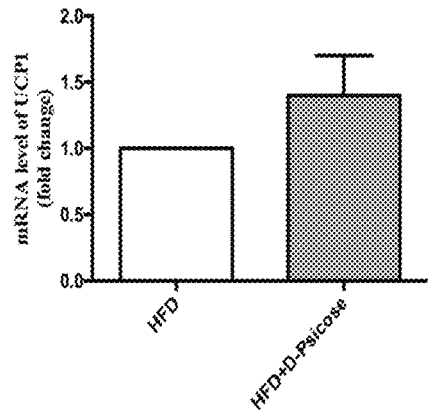

[Fig. 19]
UCP1 Protein Level in beige and brown adipose tissue
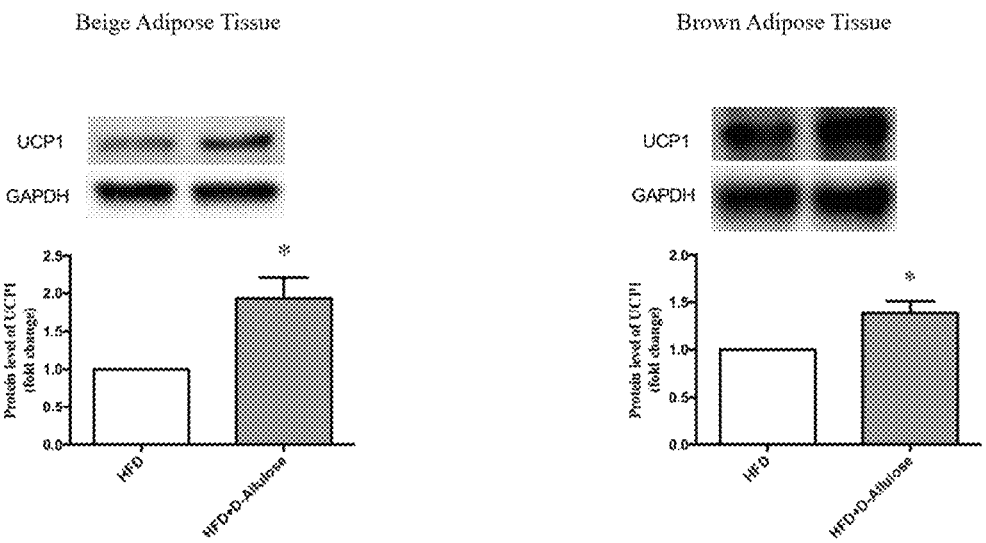
[Fig. 20]
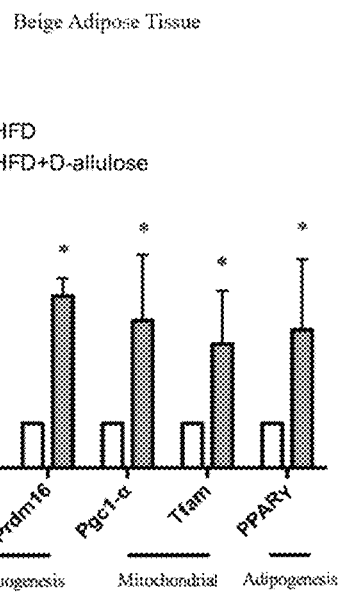
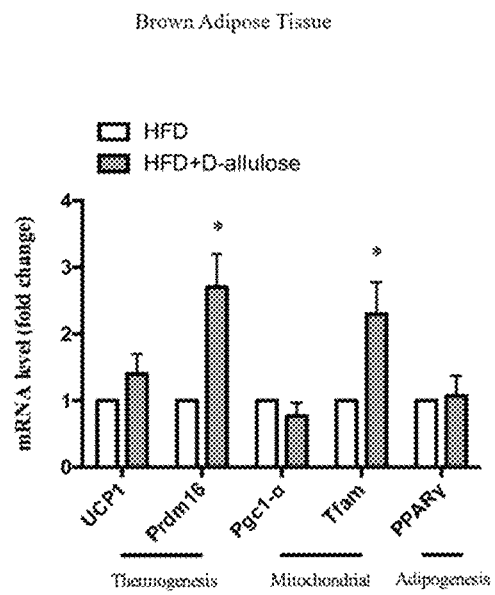

[Fig. 21]

Cell model: Beige cells

- Immortalized brown fat cells were isolated from the interscapular BAT of wild-type mice Brown adipocyte differentiation (BAT-protocol)

| Induction-1 d | Induction-1 d | Maintenance-1 d | Maintenance-1 d | Maintenance-1 d |
|---|---|---|---|---|
| 85 nM Insulin<br>1 nM T3<br>125 µM Indomethacin<br>2 µg/ml<br>500 µM IBMX | | 85 nM Insulin<br>1 nM T3 | | |

F442A white adipocyte differentiation (WAT-protocol)

| Induction-1 d | Induction-1 d | Maintenance-1 d | Maintenance-1 d | Maintenance-1 d |
|---|---|---|---|---|
| 850 nM Insulin<br>1 nM T3<br>125 µM Indomethacin<br>2 µg/ml<br>500 µM IBMX<br>1 µM Rosiglitazone | | 850 nM Insulin<br>1 nM T3<br>1 µM Rosiglitazone | | |

[Fig. 22]

Differentiation protocol

Brown adipocyte differentiation (BAT-protocol)

| Induction-1 d | Induction-1 d | Maintenance-1 d | Maintenance-1 d | Maintenance-1 d |
|---|---|---|---|---|
| 85 nM Insulin<br>1 nM T3<br>125 µM Indomethacin<br>2 µg/ml<br>500 µM IBMX<br>1 mM D-allulose (+/-) | 85 nM Insulin<br>1 nM T3<br><br><br><br>1 mM D-allulose (+/-) | | | |

F442A white adipocyte differentiation (WAT-protocol)

| Induction-1 d | Induction-1 d | Maintenance-1 d | Maintenance-1 d | Maintenance-1 d |
|---|---|---|---|---|
| 850 nM Insulin<br>1 nM T3<br>125 µM Indomethacin<br>2 µg/ml<br>500 µM IBMX<br>1 µM Rosiglitazone | 850 nM Insulin<br>1 nM T3<br><br><br><br>1 µM Rosiglitazone | | | |

[Fig. 23]
Oil Red O stain/BAT-protocol
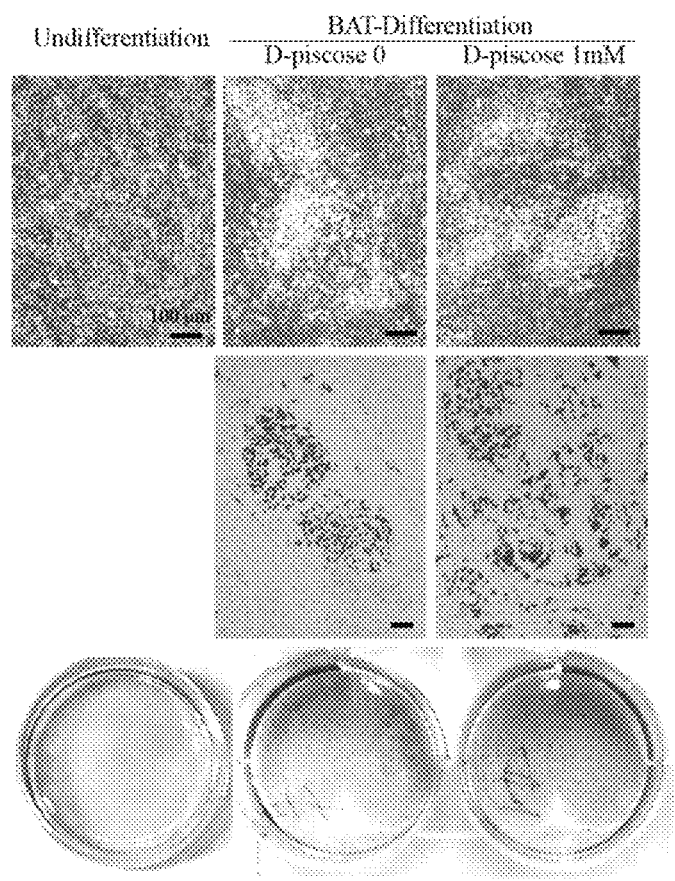

[Fig. 24]
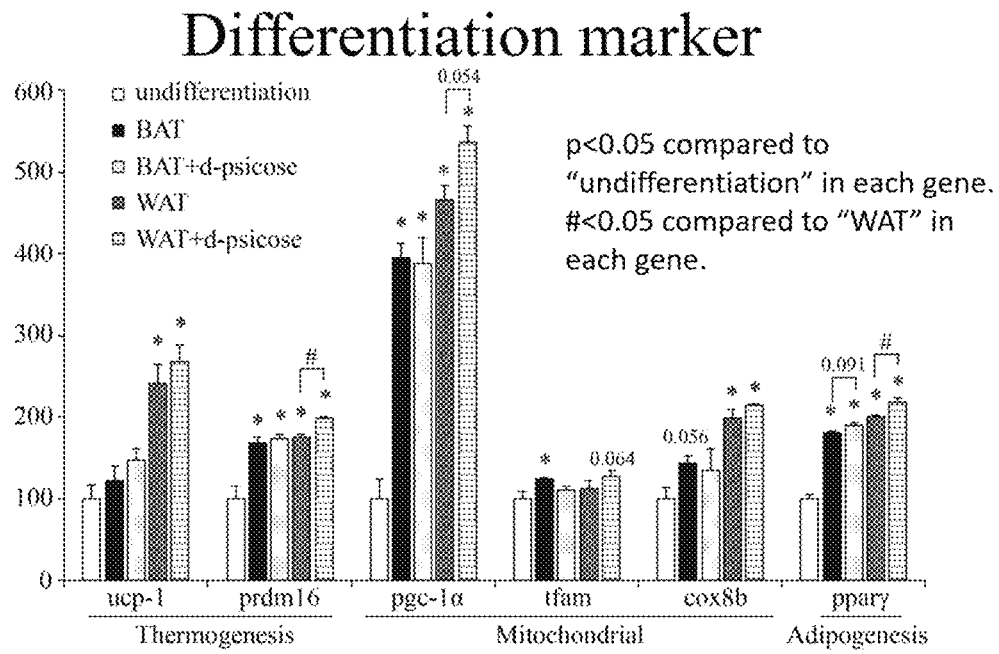
[Fig. 25]
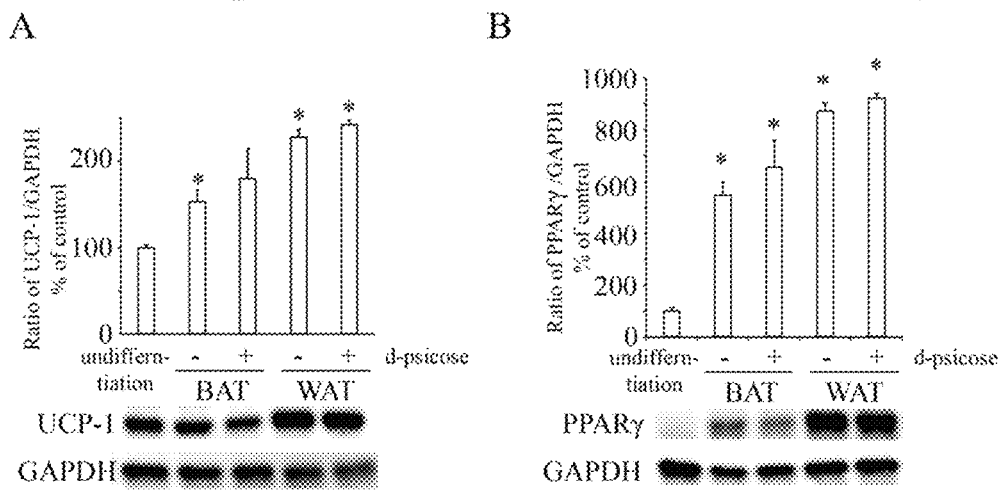

BROWN AND BEIGE ADIPOCYTE ACTIVATING AGENT CONTAINING D-ALLULOSE AS ACTIVE INGREDIENT

TECHNICAL FIELD

The present invention relates to a brown and beige adipocyte activating agent. More specifically, the invention relates to a D-allulose-containing brown/beige adipocyte activating agent.

BACKGROUND ART

Mammalian adipose tissue is classified roughly into two groups, that is, white adipose tissue and brown adipose tissue based on their function and histological characteristics. In the subcutaneous or visceral white adipose tissue, white adipocytes present therein accumulate excessive energy in the body as fat. Brown adipocytes, on the other hand, serve to burn fat and generate heat. Brown adipose tissue has a physiological role completely opposite to that of white adipocytes and it is a site where energy is consumed and dissipated as heat by sympathetic nerve stimulation or the like. Brown adipose tissue has therein brown adipocytes characterized by having multilocular lipid droplets and abundant mitochondria and UCP-1 [Uncoupling protein 1 (Uncoupling protein 1)] present in the mitochondria of brown adipocytes has a function of dissipating energy as heat. Brown adipose tissue is particularly abundant in newborns and hibernators. The main function of it is to allow animals or newborns to produce body heat without shivering. In contrast to white adipocytes containing unilocular fat droplets, brown adipocytes contain iron and therefore take on a brown color and they contain a large number of small droplets and a much higher number of mitochondria. Since brown adipose tissue requires more oxygen than most tissues, more capillaries are gathering in brown adipose tissue than in white adipose tissue. It was presumed that many brown adipocytes present in the body during infanthood were lost in adulthood. Recent studies however have revealed that as a result of PET examination, brown adipocytes which have remained around the neck or shoulder function even in adulthood.

Catechins contained in tea and the like and capsaicin contained in capsicum and the like are known to have an action of activating brown adipose tissue and there is a demand for a material highly effective for activating brown adipocytes. There are however no reports of rare sugars having an action of activating brown adipose-like cells.

PRIOR ARTS

Patent Document

Patent Document 1: International Publication No: 2010/113785

Non-Patent Documents

Non-Patent Document 1: Journal of Applied Glycoscience, Vol. 5, No. 1, 44-49 (2015)
Non-Patent Document 2: Shimomura Iichiro, et al. The Journal of the Japanese Society of Internal Medicine, 93(4), 655-661, 2004
Non-Patent Document 3: Ikeda K., et al. TEM, 2018; 29: 191-200

SUMMARY

Technical Problem

Brown adipocytes are presumed to serve to burn energy under low temperatures to warm the body and in addition, serve to increase an energy consumption amount to facilitate burning of fat.

This means that if a method of activating brown adipocytes is found, there is a possibility of this method becoming a new therapy for controlling obesity or type 2 diabetes. An object of the present invention is to provide a preparation having a high activating effect on brown adipocytes.

Another object of the present invention is to provide a composition exhibiting a UCP-1 expression promoting action and/or brown adipocyte differentiation promoting action which composition can be taken continuously for a long term without a problem of side effects. A further object of the present invention is to provide a brown adipocyte activating agent and a brown adipocyte activating food, each having D-allulose as an active ingredient.

Solution to Problem

Brown adipocytes are thought to have a function of burning energy under low temperatures to warm the body and in addition, have a function of increasing an energy consumption amount and facilitating burning of fat. Paying attention to these functions of brown adipocytes, the present inventors thought that a method of activating brown adipocytes, if any, might be a novel therapy for controlling obesity or type 2 diabetes. As a result of intensive investigation, the present inventors have obtained the finding on the activation of brown adipocytes by the administration of a rare sugar and a weight reduction due to it and completed the invention of a brown adipocyte activating agent having D-allulose as an active ingredient.

In the present invention, the term "activation of brown adipocytes" means an action of promoting the differentiation induction of brown adipose-like cells (beige adipocytes) into white adipose tissue and/or an action of promoting energy consumption in beige adipocytes or brown adipocytes and it can also be called "activation of brown adipocytes and beige adipocytes".

The present invention has, as a gist thereof, the following brown and beige adipocyte activating agents (1) to (3).
(1) A brown adipocyte and beige adipocyte activating agent having D-allulose as an active ingredient.
(2) A brown adipocyte and beige adipocyte activating agent containing at least D-allulose and having a UCP-1 expression promoting action.
(3) The brown adipocyte and beige adipocyte activating agent described in (1) or (2) which enhances UCP-1 expression and thereby activates brown adipocytes and beige adipocytes.

Further, the present invention has, as a gist thereof, the following energy consumption promoting agents (4) and (5).
(4) An energy consumption promoting agent having D-allulose as an active ingredient.
(5) The energy consumption promoting agent described in (4) which activates brown adipocytes and beige adipocytes and thereby promotes energy consumption.

Still further, the present invention has, as a gist thereof, the following UCP-1 expression enhancing agent (6).
(6) A UCP-1 expression enhancing agent having D-allulose as an active ingredient.

Still further, the present invention has, as a gist thereof, the following compositions (7) to (11).

(7) A composition containing the agent described in any of (1) to (6).
(8) A brown adipocyte and beige adipocyte activating composition having D-allulose as an active ingredient.
(9) The composition described in (7) or (8) for promoting energy consumption by thermogenesis.
(10) The composition described in any of (7) to (9) for enhancing UCP-1 expression and thereby activates brown adipocytes and beige adipocytes.
(11) The composition described in any of (7) to (10), wherein the composition is a food composition.

Advantageous Effects of Invention

The present invention makes it possible to provide a preparation having a high activation effect on brown and beige adipocytes such as brown and beige adipocyte activating agent, energy consumption promoting agent, and UCP-1 expression enhancing agent, each having D-allulose as an active ingredient.

The present invention also makes it possible to provide a composition and a food composition containing a brown and beige adipocyte activating agent, an energy consumption promoting agent, or a UCP-1 expression enhancing agent, each having D-allulose as an active ingredient. The present invention also makes it possible to provide a composition and a food composition exhibiting a UCP-1 expression promoting action and/or a brown and beige adipocyte differentiation promoting action which can be taken continuously for a long time without a problem of side effects, such as a brown and beige adipocyte activating composition having D-allulose as an active ingredient and a composition and a food composition for enhancing UCP-1 expression and thereby activating brown and beige adipocytes.

BRIEF DESCRIPTION OF DRAWINGS

FIG. 1 shows transition of body weight and transition of blood glucose level in the experiment of Example 1 using 6-week-old mice. With respect to the influence of D-allulose on the mouse body weight, a high fat diet (HFD) increased the body weight in 8-week observation. In the HFD group to which 2% D-allulose-containing water was given, a decrease in body weight was observed. Further, the blood glucose level was measured over time for 8 weeks. The HFD group showed a higher blood glucose level than the normal group. The blood glucose level of the HFD+D-allulose group decreased more than that of the HFD group.

FIG. 2 shows the size and weight of brown adipocytes under the scapula and the body weight in the experiment of Example 1 using 6-week mice.

FIG. 3 is a drawing (image of an electron micrograph) showing the pathological investigation results of brown adipose tissue in three groups. In the HFD group, compared to the normal diet group, fat deposition was observed in BA and it became white fat. On the other hand, in the HFD group+2% D-allulose group, the brown adipose tissue was morphologically comparable to that of the normal diet group, suggesting that the brown adipose tissue which had become white fat recovered to the normal brown adipose tissue.

FIG. 4 is a drawing showing an expression level of UCP-1 as the activation of brown adipocytes in the experiment of Example 1 using 6-week-old mice. In this Example, UCP-1 increased in the HFD group. It was expected that intake of a large amount of fat induced UCP-1 and calorie consumption as a defense reaction of the body. Administration of D-allulose had induced UCP-1 further. In consideration of pathological tissue together, it is presumed that the induction of UCP-1 in the HFD group is a response to a pathological condition and in the HFD group+2% D-allulose group which is morphologically normal, the activation of UCP-1 occurs as a result of activation of brown adipose tissue.

FIG. 5 is a drawing showing an expression level of PPAR-α as the activation of brown adipocytes in the experiment of Example 1 using 6-week-old mice. PPAR-α is an indicator of the activation of brown adipocytes. In the present Example, PPAR-α was induced more in the HFD group than in the normal group, which is presumed to result from the reaction of the living body due to excessive lipid intake. In the HFD group+2% D-allulose group, intake of D-allulose induced PPAR-α more strongly, suggesting that brown adipocytes are activated.

FIG. 6 is a drawing showing an expression level of PGC-1α as the activation of brown adipocytes in the experiment of Example 1 using 6-week-old mice. In the present Example, PGC-1α was induced more in the HFD group than in the normal group, which is presumed to result from the reaction of the living body due to excessive lipid intake. In the HFD+2% D-allulose group, intake of D-allulose induced PGC-1α more strongly and it is presumed that induction of PGC-1α, which is a co-activator of PPAR-α, is one of the causes of induction of UCP-1 in the downstream region and brown adipocytes are activated.

FIG. 7 is a drawing showing transition of body weight in the human clinical test of Example 2.

FIG. 8 is a drawing (extracted from Non-Patent Document 2) for describing various physiologically active materials derived from adipose tissue (adipocytokines) and their actions. Adipocytes are known not only as a storage source of energy but also as cells producing or releasing a number of cytokines (physiologically active substances). Cytokines produced or released from adipocytes are called "adipocytokines". Adipocytokines are also deeply involved in metabolic syndrome. TNF (tumor necrosis factor)-α causes phosphorylation of IRS-1 and provides insulin resistance. Adiponectin is known to have an action of suppressing obesity, diabetes, and arteriosclerosis and therefore is considered as a beneficial material. Its level becomes lower in obesity or diabetes.

FIG. 9 is a drawing for describing the action of adiponectin and possibility of using it for therapy. TNF-α is well known to be secreted from adipocytes and it is famous as a cytokine inducing insulin resistance. It is also known to suppress adiponectin which is a beneficial adipocytokine. Administration of D-allulose (D-psicose) in the present Example reduces a TNF-α level, from which it is presumed that it improves insulin resistance and improves blood glucose control.

FIG. 10 is a drawing for describing the procedure (protocol) of the experiment of Example 3. Mice are divided into two groups, with one group having five mice. Eight-week-old mice of each group are loaded with a high fat diet (HFD). From four weeks after loading with HFD, one of the groups is loaded with HFD continuously. To the other group, D-allulose (0.2 mg/body weight g/day), in addition to HFD, is administered to the stomach by a sonde. Until week 10, the body weight, food intake, water intake, and blood glucose level are monitored.

FIG. 11 is a drawing showing transition of body weight when mice were loaded with normal food and high fat diet (HFD) in Example 3.

FIG. 12 is a drawing showing transition of the body weight (BW) when mice loaded with high fat diet (HFD) were administered with D-allulose in Example 3. In the group administered with D-allulose, the body weight showed a significant decrease after week 4.

FIG. 13 is a drawing showing transition of fasting blood glucose level in Example 3. A decreasing tendency of fasting blood glucose level was observed in the D-allulose added group.

FIG. 14 is a drawing showing transition of blood glucose level in glucose tolerance test after passage of 10 weeks in Example 3. In the glucose tolerance test, the fasting blood glucose levels 90 minutes and 120 minutes after loading were significantly low.

FIG. 15 is a drawing showing food intake (on the right side) and water intake (on the left side) during the research term of Example 3. There is no significant change in the food intake and water intake between these groups, meaning no clear difference between these groups.

FIG. 16 is a drawing showing the weight and area of brown adipose tissue (BAT) standardized by the body weight when D-allulose was administered to the mice loaded with a high fat diet (HFD) in Example 3. In the group to which D-allulose was added, the weight of brown adipose tissue (BAT) was increased and the area was expanded.

FIG. 17 is a drawing for describing the distribution and function of brown adipose tissue—burn energy for thermogenesis (extracted from Non-Patent Document 3).

FIG. 18 is a drawing showing a UCP-1 mRNA expression level of beige adipocytes and brown adipocytes of mice loaded with a high fat diet (HFD), determined after administration of D-allulose thereto. On the left-side drawing, administration of D-allulose significantly increases the expression level of UCP-1 in beige adipocytes. On the right-side drawing, the expression level of UCP-1 is increased also in classical brown adipose tissue.

FIG. 19 is a drawing showing an expression level of UCP-1 protein in beige adipocytes and brown adipocytes of the mice loaded with high fat diet (HFD), determined after administration of D-allulose thereto. Administration of D-allulose significantly increases the expression level of UCP-1 protein in the beige adipocytes. The expression level of UCP-1 protein is increased also in the classical brown adipose tissue.

FIG. 20 is a drawing showing, with regards to the induction of beige adipocytes and activation of brown adipocytes caused by D-allulose administration, expression levels, each of UCP-1 and Prdm16 which are genes involved in thermogenesis, Pgcl-α and Tfam which are genes reflecting the mitochondrial function of organelle involved in thermogenesis, and PPARγ which is a gene involved in differentiation of fat.

FIG. 21 is a drawing for describing, with regard to an experiment using cells (a single-clone-derived cell strain is established from BAT of adult supraclavicular fossa portion and is used as a research model of differentiation induction into beige adipocytes), two protocols, that is, BAT-protocol and WAT-protocol, for inducing beige adipocytes.

FIG. 22 is a drawing for describing, in an experiment using cells, protocols including two protocols, that is, BAT-protocol and WAT-protocol, for inducing beige adipocytes and further including addition of D-allulose.

FIG. 23 is a drawing (an image of an electron micrograph) showing, by fat staining, that addition of D-allulose to the differentiation inducing protocol promotes induction into beige adipocytes.

FIG. 24 is a drawing showing the results of investigating the expression of various markers (UCP-1, Prdm16, Pgc-1α, tfam, cox8b, and PPARγ) as evaluation of beige adipocytes induced by the differentiation inducing protocol. The WAT-protocol has a stronger influence on the induction of browning marker genes (UCP-1, Pgc-1α, and cox8b). When the WAT-protocol is used, D-allulose enhances the expression of Prdm16, Pgc-1α, and PPARγ. In both differentiation protocols, D-allulose enhances the expression of PPARγ, suggesting that D-allulose promotes adipogenesis.

FIG. 25 is a drawing showing the investigation results of the expression of UCP-1 and PPARγ in the presence or absence of D-allulose as evaluation of beige adipocytes induced by the protocol. The expression of UCP-1 and PPARγ is increased in the presence of D-allulose, showing that induction of beige adipocytes is promoted. Compared to the BAT-protocol, the WAT-protocol has a higher effect on the induction of UCP-1 protein expression. When the WAT-protocol is used, D-allulose slightly enhances the expression of UCP-1 protein.

DESCRIPTION OF EMBODIMENTS

[Brown Adipocytes]

In the present invention, the term "brown adipocyte" means both a classical brown adipocyte formed in the fetal period and a brown adipose-like cell induced to differentiate into white adipose tissue (may also be called "beige adipocyte" or bright cell). In other words, in the present invention, not only a classical brown adipocyte in the narrow sense but also a brown-like adipocyte induced into white adipose tissue is called "brown adipocyte". A brown-like adipocyte induced into white adipose tissue may particularly be called "beige adipocyte" or "brown adipose-like cell".

[White Adipocytes]

White adipocytes have large unilocular lipid droplets and do not have much cytoplasm. Brown adipocytes, on the other hand, have morphological or histological characteristics that they have small multilocular lipid droplets, have a large number of mitochondria around these multilocular lipid droplets, giving a unique brown appearance, and are rich in sympathetic nerves and blood vessels. White adipocytes and brown adipocytes can therefore be distinguished by morphological or histological observation of cells. Another difference is that white adipose stores energy, while brown adipocytes consume or dissipate energy as heat. In addition, brown adipocytes have higher energy metabolism than white adipocytes and release energy as heat so that their glucose uptake increases. The presence of brown adipocytes can therefore be evaluated, for example, by measuring the accumulation of 18F-labeled glucose by PET (positron emission tomography). Further, in brown adipocytes, since a 33 kDa protein called "uncoupling protein 1 (UCP-1)" is specifically expressed in the inner mitochondrial membrane in them, presence of brown adipocytes can be confirmed by measuring the expression of UCP-1 mRNA or UCP-1 protein.

[Beige Adipocytes]

The morphological characteristics of beige adipocytes are similar to those of brown adipocytes. They have multilocular lipid droplets therein and are rich in mitochondria which have expressed a specific protein UCP-1. They are contrast to white adipocytes having unilocular lipid droplets and poor in cytoplasm. From the standpoint of functional characteristics, different from white adipocytes which store excess energy as neutral fat, brown adipocytes and beige adipocytes achieve thermogenesis by uncoupling of oxidative phosphorylation by UCP-1. Beige adipocytes are similar to brown adipocytes in these points, but they are rather close to white adipocytes in the following points. First, with respect to a site, brown adipocytes of mice form a cell cluster in the interscapulum or around the kidney and are present therein, while beige adipocytes inductively and scatteringly appear in white adipose tissue at the groin or the like. This phenomenon is called "browning of white fat". Next, with respect to a generation source, brown adipocytes are derived from muscle precursor cells expressing Myogenic factor 5 (Myf5), which is common with skeletal muscle, while beige adipocytes are, similar to white adipocytes, derived from precursor adipocytes which are Myf5-negative and express a plate-derived growth factor receptor α (PDGFRα) or smooth muscle actin (SMA). Thus, beige adipocytes have both characteristics similar to those of brown adipocytes and white adipocytes and characteristics contrary thereto so that they are presumed to be not white adipocytes with altered properties but third adipocytes.

Brown adipocytes and beige adipocytes contribute to maintenance of body temperature under a cold environment as special adipocytes which produce heat in response to cold exposure. The thermogenesis or energy consumption activities of these adipocytes are expected to be useful not only for body temperature regulating ability but also for prevention of obesity or metabolic diseases. It has been revealed that although brown adipocytes and beige adipocytes express an uncoupling protein (UCP-1) and have heat generating ability in common, they are different in the origin of cells or function control mechanism. In particular, the fact that brown adipose tissue (BAT) of human adult is mainly made up of beige adipocytes is presumed to be important in searching for an obesity prevention method with BAT as a target.

In the present invention, the term "activation of brown adipocytes" means an action of promoting differentiation induction of brown adipose-like cells (beige adipocytes) into white adipose tissue and/or an action of promoting energy consumption in beige adipocytes or brown adipocytes. The activation of brown adipocytes may particularly include enhancement of metabolism in beige adipocytes or brown adipocytes, promotion of energy consumption, and conversion of a fatty acid into thermal energy. The conversion of a fatty acid into thermal energy may be performed by UCP-1. As described above "the activation of brown adipocytes" may be expressed as "activation of brown adipocytes and beige adipocytes".

The term "brown adipocyte activating agent" means a material having a brown adipocyte activating action as described above. As described above, the presence of brown adipocytes and/or an increase in energy metabolism of brown adipocytes can be assessed by measuring expression of UCP-1 mRNA or UCP-1 protein, histologically observing adipocytes, measuring the accumulation of 18F-labeled glucose by PET, measuring cold-induced thermogenesis, or the like. In addition, the differentiation induction of brown adipose-like cells (beige adipocytes) into white adipose tissue may be called "reactivation of brown adipocytes" particularly.

The brown adipocyte activating agent of the present invention can promote energy metabolism by thermogenesis. Energy metabolism includes that by basal metabolism, that by exercise, that by daily living activities, and that by thermogenesis. In daily energy consumption, basal metabolism accounts for about 60%, exercise for about 5%, daily living activities for about 24%, and thermogenesis for about 10%. Many attempts have been made to enhance energy metabolism by increasing muscles to enhance basal metabolism or by briskly conducting exercise or daily living activities. On the other hand, energy consumption by thermogenesis is conducted in order to adapt the body to a sudden temperature change and it increases for example by cold stimulation. It is also known that thermogenesis is increased by food intake or thermogenesis is caused for generating heat to counter infection or inflammation. In the present application, therefore, the term "energy consumption by thermogenesis" means metabolic energy consumption consumed for thermogenesis for responding to cold stimulation, food intake or the like, not depending on basal metabolism, muscle exercise, or the like. The brown adipocyte activating agent of the present invention may particularly stimulate the sympathetic nerve to enhance the thermogenesis in beige adipocytes or brown adipocytes and thereby promoting energy metabolism. Such thermogenesis may occur due to conversion of a fatty acid into thermal energy and the conversion of a fatty acid into thermal energy may be performed by UCP-1.

The brown adipocyte activating agent, energy consumption agent, and the like and compositions containing them according to the present invention may enhance energy metabolism or may enhance UCP-1 expression not in the liver or muscle but in brown adipose tissue.

Although the content of D-allulose in the brown adipocyte activating agent, UCP-1 expression enhancing agent, or the like according to the present invention is not particularly limited, it is blended in an intake amount preferably from 0.3 to 50 g per day in terms of weight. In some cases, it is blended in an amount of from 0.3 to 5 g, from 0.5 to 3 g, from 1.5 to 4.5 g, from 0.5 to 5 g, from 0.5 to 50 g, from 0.5 to 20 g, or the like. To enhance the advantage of the present invention, another brown adipocyte activating agent, body-temperature loss suppressant, energy consumption promoting agent, UCP-1 expression enhancing agent, metabolism promoting agent, or the like may be used in combination.

Although the intake amount of D-allulose is not particularly limited, it is blended, for a human having a body weight of 60 kg, in an intake amount preferably from 0.3 to 50 g per day in terms of weight. In some cases, it is preferred to take it in an amount of from 0.3 to 5 g, from 0.5 to 3 g, from 1.5 to 4.5 g, from 0.5 to 5 g, from 0.5 to 50 g, from 0.5 to 20 g, or the like.

The method of producing a brown adipocyte activating agent according to the present invention may include a step of producing D-allulose. The form of D-allulose to be used in the present invention is arbitrary insofar as it does not damage the advantage of the present invention as in the above. At present, it is the common practice to use a method of treating fructose with an enzyme (epimerase) as a method for obtaining rare sugar, D-allulose. Alternatively, it can be obtained by a method (Patent Document 1) of using a rare sugar syrup or isomerized sugar as a raw material and treating with a system having one or more selected from the group consisting of basic ion exchange resins, alkalis, and calcium salts. It is produced so as to mainly contain D-allulose and D-allose and it contains from 0.5 to 17 mass % D-allulose, from 0.2 to 10 mass % D-allose, and other unidentified rare sugars. A rare sugar syrup (product name: Rare Sugar Sweet) thus produced has glucose and fructose as main ingredients and it contains 5.4 g/100 g of D-psicose, 5.3 g/100 g of sorbose, 2.0 g/100 g of tagatose, 1.4 g/100 g of allose, and 4.3 of mannose (Non-Patent Document 1). Rare sugars such as D-psicose can be produced by making use of an enzyme method, alkali method, or the like but it has been found that they are contained in plants such as leaves of Zuina.

The present invention also provides a composition containing the above-described brown adipocyte activating agent (brown adipocyte and beige adipocyte activating agent), body temperature loss suppressant, energy consumption promoting agent, or UCP-1 expression enhancing agent. The composition of the present invention can be provided in various forms such as powder, liquid, solid, granule, tablet, paste, gel, milky lotion, cream, sheet, spray, and foam.

The food composition of the present invention may be provided as powder, beverage, or tablet. The food composition of the present invention may also be a dry powder, beverages such as tea and soft drinks, tablets and capsules such as supplements, processed foods such as retort foods, luxury items such as desserts, seasonings, dairy products, and fat and oil processed foods. It may be provided in various forms such as powder, liquid, solid, granule, granule, paste and gel. Furthermore, the food composition of the present invention is not only food for humans but also feed for other animals such as livestock.

Although the content of the brown adipocyte activating agent (brown adipocyte and beige adipocyte activating agent) in the composition of the present invention is not particularly limited, the dose is preferably from 0.3 to 50 g a day in terms of D-allulose (D-psicose) when administered orally to adult. This dose can be increased or decreased as needed, depending on the age or symptom. The daily dose of the brown adipocyte activating agent, energy consumption promoting agent, or UCP-1 expression enhancing agent according to the present invention is preferably administered once a day, in two or three portions a day with an appropriate interval, or before, after, or with a meal. In the composition of the present invention containing D-allulose (D-psicose), D-allulose (D-psicose) is blended so as to be contained in the composition in an amount of from 0.1 to 50 wt. %, preferably from 0.5 to 30 wt. %, more preferably from 1 to 10 wt. %. When the amount of D-allulose (D-psicose) in the composition is less than 0.1 wt. %, the resulting composition has insufficient brown adipocyte activating action. An amount of D-allulose (D-psicose) exceeding 50 wt. % in the composition is not preferred from an economical point of view.

The composition of the present invention may further contain another material having a brown adipocyte activating action, a body temperature loss suppressing action, an energy consumption promoting action, or the like in order to further enhance the brown adipocyte activating action, body temperature loss suppressing action, energy consumption promoting action, or the like.

Further, the composition of the present invention can be used in combination with an arbitrarily selected additive if necessary. As the additive, an excipient or the like can be incorporated.

As the excipient, any excipient can be used insofar as it is usually used for preparing the composition in a desired form. Examples include starches such as wheat starch, rice starch, corn starch, potato starch, dextrin, and cyclodextrin, crystalline celluloses, saccharides such as lactose, glucose, sugar, reduced maltose, starch syrup, fructooligosaccharide and emulsified oligosaccharide, and sugar alcohols such as sorbitol, erythritol, xylitol, lactitol, and mannitol. These excipients may be used either singly or in combination of two or more.

The composition of the present invention may further contain, if necessary, other ingredients selected as needed from known ones and examples of usable ones include colorants, preservatives, thickeners, binders, disintegrants, dispersants, stabilizers, gelling agents, antioxidants, surfactants, preservatives, pH regulators, oils, powders, coloring materials, water, alcohols, thickeners, chelating agents, silicones, antioxidants, UV absorbers, humectants, flavoring agents, various medicinal ingredients, antiseptics, pH regulators, and neutralizers.

The brown adipocyte activating agent (brown adipocyte and beige adipocyte activating agent) of the present invention can prevent and/or suppress obesity by promoting metabolism by taking an approach of inducing the differentiation of brown adipose-like cells (beige adipocytes) into white adipose tissue and/or activating beige adipocytes or brown adipocytes to promote systemic energy consumption using thermogenesis. It is therefore effective for the treatment and/or prevention of diseases caused by obesity. In addition, cooling of the body can be prevented or energy metabolism by diet can be enhanced by activating brown adipocytes to enhance cold-induced thermogenesis or enhance diet-induced thermogenesis, respectively. Furthermore, with respect to the safety of D-allulose (D-psicose) serving an active ingredient of the present invention, since it is contained in various foods we take (cola, castella, maple syrup, and the like) and it is not a material that our bodies take for the first time, it is presumed that there is no major risk in taking rare sugar D-allulose (D-psicose).

EXAMPLES

The present invention will next be described in further detail by Examples. It is to be noted that the present invention is not limited to or by them.

[Confirmation method of brown adipocytes] The presence of brown adipocytes can be confirmed by a known method. Examples of it include staining with a fluorescent dye capable of detecting lipid droplets in cells and detection of a gene product (mRNA or protein) expressed in brown adipocytes. Examples of the fluorescent dye capable of detecting lipid droplets in cells include Oil Red O and BODIPY. Examples of the gene product expressed in brown adipocytes include UCP-1, CIDEA, PGC-1α, and PPAR-α. Of these, UCP-1 is a particularly preferred one as an indicator of brown adipocytes because it is thought to be a gene which is specifically expressed in brown adipocytes, encodes a mitochondrial inner membrane protein that uncouples oxidative phosphorylation, and works as the basis of the function of brown adipocytes.

In Examples of the present invention, activation of brown adipocytes was evaluated by the expression level of UCP-1, PPAR-α, or PGC-1α.

The terms used in Examples of the present invention will next be described briefly. Refer to various adipose tissue-derived physiologically active substances (adipocytokines) and actions thereof (extracted from Non-Patent Document 2) in FIG. 8 and actions of adiponectin and its using possibility for therapy in FIG. 9.

[BAT]

Brown adipose tissue (BAT) or brown adipocytes are one of two types of fat or adipose tissue found in mammals. The other type is white adipose tissue. Brown adipose tissue is particularly abundant in newborns and hibernators. The main function of it is to allow animals or newborns to generate body heat without shivering. In contrast to white adipocytes containing unilocular lipid droplets, brown adipocytes contain iron and therefore take on a brown color and they contain a large number of small droplets and a much higher number of mitochondria. Since brown adipose tissue requires more oxygen than most tissues, more capillaries are gathering in brown adipose tissue than in white adipose tissue.

When noradrenaline binds to a β3 receptor on brown adipocytes, UCP-1 (uncoupling protein) is formed, uncoupling occurs in mitochondria, and heat is generated. This is means for thermogenesis not caused by exercise and it is often found during hibernation of animals.

Brown adipocytes are found most in babies because they keep their body temperature, that is, they save their lives. When adults are placed under severe coldness, they shiver. They produce heat by moving their muscles in such a manner, but babies cannot control their body temperature by themselves because they have few muscles. Babies have many brown adipocytes for keeping their life but after that, they do not need them, resulting in a gradual decrease in the number of the adipocytes. BMI increases with aging. The number of brown adipocytes decreases on the contrary and it causes obesity. This means that a body weight is likely to increase when brown adipocytes, which are also called "fat that burns fat", disappears. Increasing the number of brown adipose tissue or enhancing their function is expected to lead to a new therapy of 2 type diabetes or obesity.

[UCP-1]

Uncoupling protein is often abbreviated as UCP, which is an acronym for Uncoupling protein. Uncoupling protein (UCP) is a mitochondrial inner membrane protein capable of consuming a transmembrane proton gradient before production of oxidative phosphorylation energy. In mammals, five types, that is, UCP-1 to UCP-5 are known. It uses energy for producing heat instead of producing ATP so that an uncoupling protein plays a normal physiological function such as thermogenesis during hibernation not caused by exercise. UCP-1 is present only in brown adipocytes, UCP-2 is recognized in white adipocytes, immune-system cells, nerve cells, and the like, and UCP-3 is present much manly in skeletal muscle and muscle tissue of heart or the like. A remarkable decrease in the synthesis of UCP-3 protein in the skeletal muscle of diabetic patients has suggested that it is associated with thermogenesis or fat metabolism. When noradrenaline binds to a β3 receptor on brown adipocytes, UCP-1 is produced, uncoupling occurs in mitochondria, and heat is produced. Yellow races including Japanese tend to have genetic mutation in the gene of their β3 receptor. Since this mutated gene does not produce heat much but saves calories and do not consume them easily, it may be called "thrifty gene".

Mitochondria uncoupling protein (UCP) has a function of uncoupling the oxidative phosphorylation reaction in the mitochondrial inner membrane and dissipating energy as heat. About the most representative UCP (UCP-1) of brown adipose tissue, the following facts are known: (1) obese animals have a reduced UCP-1 function; (2) animals that eat much but do not become obese has increased UCP-1; and mice having artificially reduced UCP-1 expression become obese, while high-expression mouse become thin. Activation of UCP-1 is expected to bring about an anti-obesity effect and therefore drugs or foods for it have been searched for. The representative example of them is an adipocyte-specific adrenergic receptor agonist. In fact, a β-agonist promotes lipolysis in white adipocytes and at the same time activates UCP-1 to convert a liberated fatty acid to heat and eventually decrease the body fat. Different from mice and the like, adults have only a small amount of brown adipose tissue. When administration of β-agonist is continued, however, normal adipocytes are converted into brown ones, leading to an increase in UCP-1. Further, proteins UCP-2 and UCP-3 homologous to UCP-1 are widely present in the human skeletal muscle, white adipose tissue, and the like so that UCP including them are presumed to be one of the target molecules for antiobesity.

[PGC-1α]

Involvement of PGC-1α in promotion of glucose metabolism by exercise: in the skeletal muscle which has continued exercise to some extent, the number of intracellular organelles called "mitochondria" increases, fat burns briskly, a glucose transporter GLUT4 that introduces glucose in the blood (blood glucose) into the skeletal muscle increases and as a result, glucose metabolism becomes active. PGC-1α which is a material controlling the gene transcription has a function of promoting synthesis of mitochondria and in an experiment using skeletal muscle cultured cells, it increases GLUT4. PGC-1α is also present in skeletal muscle and its amount increases by exercise so that an increase in the amount of PGC-1α is presumed to lead to a change in the properties of skeletal muscle. PGC-1α is a coactivator of PPAR-α, PPAR-γ, and other transcriptional regulatory elements. It is expressed not only in muscle but also in the liver or brown adipose tissue. Its expression increases during fasting and promotes gluconeogenesis in the liver, while it regulates a transcription program relating to adaptation to thermogenesis in brown adipose tissue. Introduction of PGC-1α into white adipocytes causes a brown adipocyte-like change such as enhancement of mitochondrial biosynthesis or enhancement of UCP-1 expression. Full-length PGC-1α is 113 kDa and is induced in brown adipocyte tissue by cold exposure, in the liver and kidney by fasting, and in the skeletal muscle by exercise.

[PPAR-α]

PPAR-α is a member of an intranuclear receptor superfamily. Three subtypes, that is, α, γ, and δ (β) have been reported to date. Since it was activated by a fibrate type drug which was a peroxisome proliferator, the a subtype (PPAR-α) discovered first had such a name. It is regarded as a transcription factor group closely related to intracellular metabolism of hydrocarbon, lipid, protein, or the like and cell differentiation. These subtypes each form a heterodimer with a retinoid X receptor (RXR) and bind to a PPAR responses element (PPRE). PPAR-α is strongly expressed in the liver, brown adipose tissue, heart, and kidney, is activated with a free fatty acid or the like as a physiological ligand, and causes a reduction in blood triglyceride concentration or the like. Examples of an exogenous ligand include so-called fibrate-based drugs such as bezafibrate and clofibrate. Most of target genes are those related to lipid metabolism and become a main target of a hypertriglyceridemia improving drug.

[Prdm16]

Prdm16 is a transcription factor having an important role as a switch for inducing differentiation into brown adipocytes and beige adipocytes. Prdm16 forms a complex with C/EBPβ and because of having methyl group transfer activity, it induces differentiation from Myf5-positive cells into brown adipocytes. As only one histone methylation enzyme involved in methyl group transfer activity of Prdm16 transfer complex, lysine methyl transferase EHMT1 was identified. The Prdm16 and EHMT complex plays a role of suppressing the expression of a skeletal muscle-related gene in mouse BAT and starting a gene program for differentiating precursor brown adipocytes to brown adipocytes. In addition, Prdm16 also has a function of suppressing the expression of white adipose-related genes such as resitin and inducing beige adipose-related gene program. It therefore plays a very important role as a switch for differentiating precursor adipocytes to beige adipocytes.

[Tfam]

A mitochondrial transcription factor A (Mitochondrial transcription factor A: TFAM) was purified and cloned as a transcription factor of mitochondrial DNA by Clayton et al. TFAM is a protein belonging to the hight mobility group (HMG) family proteins and like many HMG family proteins, it can bind to DNA regardless of DNA sequence. There is a correlation between the amount of change in TFAM and the amount of mitochondrial DNA. The replication of mitochondrial DNA depends on the transcription. So that an expression level of TFAM is used as a substitute of function evaluation of mitochondria. Mitochondria are involved in most of ATP production through oxidative phosphorylation and are a center of energy metabolism in the living body.

[Adipocytokine]

It is a generic name of physiologically active substances secreted from adipocytes.

[Leptin]

It is a hormone secreted from adipocytes. It has a function of suppressing appetite and activating energy metabolism.

[HbA1c]

HbA1c is a substance in which Glucose binds to hemoglobin (Hb) present in erythrocytes. Erythrocytes have a life span of about 4 months and during this term, they circulate in the body and glucose binds to hemoglobin. The higher the blood glucose level, the higher an HbA1c level (hemoglobin A1c). The HbA1c level reflects the blood glucose control level in the past 1 to 2 months.

[GA]

Glycoalbumin is a glycated protein reflecting the state of blood glucose. It is used as an indicator of blood glucose control in the past 1 to 2 weeks.

[Adiponectin]

It is a secretory protein secreted from adipocytes. Its blood level is much higher than that of general hormones and reaches μg/ml order. It has a variety of actions such as a sugar uptake promoting action without using an insulin receptor, burning of a fatty acid, an action of reducing a fatty acid in cells and enhancing the sensitivity of an insulin receptor, enhancement of insulin sensitivity by activating the AMP kinase in the liver, arteriosclerosis suppression, anti-inflammatory, and myocardial hypertrophy suppression. It is a beneficial adipocytokine.

[TNF-α]

Adipose tissue secretes inflammatory cytokines and TNF-α causes impairment of glucose uptake into cells or reduction in sensitivity to insulin. In addition, it has been reported that TNF-α promotes production of a fatty acid in adipocytes or hepatocytes and causes anti-glycerinemia mainly through TNFR1. It is one of adipocytokines (physiologically active substances) secreted from adipocytes and has an action of suppressing the action of sugar in muscle, adipose tissue, or liver. It increases during obesity and increases the risk of diabetes or arteriosclerosis. It is secreted from adipocytes and famous as a cytokine causing insulin resistance.

[MCP-1]

It is an important factor that is secreted from an inflammatory layer (vascular endothelial cells, adipocytes), induces monocyte migration, differentiation into macrophage, and expression of an oxidized LDL receptor, and forms arteriosclerosis. Administration of D-psicose for 3 months causes a significant decrease in MCP-1 concentration, suggesting that D-psicose has an anti-arteriosclerotic action.

[Oxidized LDL Receptor]

An LDL (low specific gravity lipoprotein) receptor family is a multifunctional protein responsible for intracellular uptake of various ligands including LDL or for signal transduction. It has been revealed that when LDL is oxidized into oxidized LDL by an oxidizing substance such as free radical, it is not recognized by a normal LDL receptor but is recognized by a macrophage scavenger receptor and taken up infinitely to cause foaming of a macrophage.

EXAMPLE 1

The influence of administration of D-allulose, one of rare sugars, on brown adipocytes (BAT: abbreviation of brown adipose tissue) was studied. The experiment was performed using 6-week mice and the mice were divided into 3 groups, each group having 5 mice. The treatment was made as follows for 8 weeks.

1. Protocol:
   (1) A group of normal diet and drinking of water (Normal food)
   (2) A group of high fat diet and drinking of water (HFD)
   (3) A group of high fat diet and drinking of water containing 2% D-allulose (D-allulose) (HFD+2% D-allulose)
2. Evaluation item:
   (1) Transition of Body Weight
   Transition of Blood Glucose
   (2) Size and weight of brown adipocytes under the scapula
   (3) Pathological evaluation of the morphological change in brown adipocytes
   (4) Evaluation of UCP-1, PPAR-α, and PGC-1α expression levels as activation of brown adipocytes
3. Results
1) Results of Transition of Body Weight and Transition of Blood Glucose are Shown in FIG. 1.

In the group loaded with high fat diet, body weight increased. In the high fat diet and D-allulose group (HFD+2% D-allulose), a decrease in body weight was observed as compared with the high fat diet group. With regard to the transition of blood glucose, the blood glucose was high in the high fat diet group, but a decrease in blood glucose was recognized in the high fat diet and D-allulose group.

2) The Results of the Size and Weight of Brown Adipocytes Under the Scapula and the Body Weight are Shown in FIG. 2.

In the group loaded with high fat diet, brown adipocytes decreased. In the high fat diet and D-allulose group, an increase in brown adipocytes was recognized as compared with the high fat diet group.

3) Pathological evaluation results of a morphological change of brown adipocytes are shown in FIG. 3.

Also in tissue staining, steatosis was recognized in the high fat diet group, but the high fat diet and D-allulose group (HFD+2% D-allulose) was improved to have almost a normal state.

4) Evaluation Results of the Activation of Brown Adipocytes in Terms of UCP-1, PPAR-α, and PGC-1α Expression Levels are Shown in FIG. 4, FIG. 5, and FIG. 6, Respectively.

In the high fat diet and D-allulose group (HFD+2% D-allulose), marker gene expression enhancement of brown adipocytes was recognized as compared with the high fat diet group.

Summary:

As shown in FIG. 1, with respect to the influence of D-allulose on the body weight of mice, the high fat diet (HFD) increased the body weight as a result of 8-week observation. In the HFD group to which 2% D-allulose-containing water was given, a decrease in body weight was observed. Further, the blood glucose level was measured over time for 8 weeks. The HFD group showed a higher blood glucose level than the normal group. The blood glucose level of the HFD+D-allulose group became lower than that of the HFD group.

As shown in FIG. 2 showing the size and weight of brown adipocytes under the scapula and the body weight in the experiment of the this Example using 6-week mice and FIG. 3 showing the pathological investigation results of brown adipose tissue in three groups, fat deposition and whitening of BAT were recognized in the HFD group as compared with the normal diet group. In the HFD+2% D-allulose group, on the other hand, the brown adipose tissue was morphologically comparable to that of the normal food group, revealing that the whitened brown adipose tissue was recovered to normal brown adipose tissue.

As shown in FIG. 4 showing the activation of brown adipocytes in terms of the expression level of UCP-1, UCP-1 increased in the HFD group. It was expected that along with intake of a large amount of fat, UCP-1 was induced and calories were consumed as a defense reaction of the living body. Administration of D-allulose induced UCP-1 further. Considering this together with pathological tissue, the induction of UCP-1 in the HFD group is a response to a pathological condition, while in the HFD+2% D-allulose group having morphologically normal tissue, the activation of UCP-1 is presumed to result from differentiation and proliferation of brown adipose tissue.

As shown in FIG. 5 showing the activation of brown adipocytes in terms of an expression level of PPAR-α in which PPAR-α is an indicator of the activation of brown adipocytes, PPAR-α was induced more than in the HFD group than in the normal group, which is presumed to be a biological reaction due to excessive lipid intake. In the HFD+2% D-allulose group, PPAR-α was induced more strongly by the D-allulose intake, which is presumed to result from the activation of brown adipocytes.

As shown in FIG. 6 showing the activation of brown adipocytes in terms of an expression level of PGC-1α, PGC-1α was induced in the HFD group than in the normal group, which is presumed to result from the biological reaction due to excessive lipid intake. In the HFD+2% D-allulose group, PGC-1α was induced more strongly due to D-allulose intake. Induction of PGC-1α which is a coactivator of PPAR-α is presumed to be one of the causes of the induction of UCP-1 in the downstream region, suggesting the activation of brown adipocytes.

It is considered that the administration of D-allulose stimulated the activation of brown adipocytes and it enhances thermogenesis acceleration, fat burning, and metabolism acceleration to contribute to a reduction in body weight. As a future prospect, this shows the possibility that intake of D-allulose enables acquisition of a constitution "easy to lose weight".

EXAMPLE 2

The effect of rare sugar D-psicose (D-allulose) on type 2 diabetic patients was studied.
[Method]
<Selection Standards>
Type 2 diabetic patients unable to get sufficient effects by any of the following treatments (HbA1c: 6.5% or more) (prediabetes)
1) Only diet therapy and exercise therapy
2) Drug therapy in addition to diet therapy and exercise therapy
<Exclusion Standards>
1) Patients having a contraindication to D-allulose (D-psicose) administration
2) Patients who are participating in another clinical trial
3) Pregnant women, parturients, lactating women, or women who may be pregnant
4) Patients having 8% or more HbA1c and poor in blood glucose control
5) Patients recognized to have severe renal dysfunction (serum creatinine level: 1.5 mg/dl or more)
6) Patients having another severe complication
<Experimenting Method>
D-allulose (D-psicose) powders: provided as sticks each containing 5 g/pack (product of Rare Sweet)
It was orally administered with 5 g per dose three times a day.
Twelve type 2 diabetic patients (4 male cases, 8 female cases) who could be observed for 3 months were compared for general findings and blood test before administration and 12 weeks after administration (Wilcoxon signed rank test).
The experiment was performed after approved by the Ethics Committee, Faculty of Medicine, Kagawa University which complied with Helsinki Declaration and the ethical guideline for clinical research.
<Discussion>
In the test conducted above, D-allulose (D-psicose) was administered for 3 months. A significant decrease in body weight was recognized after 3 months.
With regard to various physiologically active substances derived from adipose tissue (adipocytokines) and actions thereof, neither leptin nor adiponectin showed a significant change for 3-month D-psicose administration term.
As is well known, TNF-α is famous as a cytokine secreted from adipocytes and inducing insulin resistance. It is also known to suppress adiponectin which is a beneficial adipocytokine. Administration of D-psicose in the present Example reduces a TNF-α level, which is presumed to improve insulin resistance and improve blood glucose control.
MCP-1 is an important cytokine that is secreted from an inflammatory layer (vascular endothelial cells, adipocytes), induces monocyte migration, differentiation into macrophage, and expression of an oxidized LDL receptor, and forms arteriosclerosis. Administration of D-allulose (D-psicose) for 3 months causes a significant decrease in MCP-1 concentration, suggesting that D-allulose (D-psicose) has an anti-arteriosclerotic action.
<Conclusion>
(1) Twelve type 2 diabetic patients (4 male cases, 8 female cases) were orally administered with 5 g/once of D-allulose (D-psicose) three times a day and their general findings and blood test before administration and for 12 weeks after administration were compared.
(2) No significant difference was found among HbA1c, GA, leptin, and adiponectin.

(3) The TNF-α and MCP-1 levels significantly decreased after administration, compared with the levels before administration. In particular, the TNF-α level showed a significant decrease in 2 months after administration.
(4) The body weight decreased by 1 kg on average in 3 months after administration.
(5) D-allulose (D-psicose) has the possibility of being useful for administration to type 2 diabetic patients.

EXAMPLE 3

As in Example 1, with regard to the influence of D-allulose (D-allulose) administration on brown adipocytes (BAT: abbreviation of Brown adipose tissue), the effect of the differentiation induction of beige adipocytes on body weight reduction and body fat reduction was studied.

(Purpose) The influence of D-allulose administration to mice on their brown adipose tissue is confirmed. In addition, differentiation of beige adipocytes is studied with a change in UCP-1 expression or the like as a marker.

1. Protocol:

Mice are divided into two groups, each group having five mice. Eight-week-old mice of each group are loaded with a high fat diet (HFD). From four weeks after loading with HFD, one of the groups is loaded with HFD continuously. To the other group, D-allulose (0.2 mg/body weight g/day) together with HFD is administered to the stomach by a sonde. Until week 10, the body weight, food intake, water intake, and blood glucose level are monitored.

2. Results

1) The results of a body weight increase at the time of loading with a high fat diet (HFD) are shown in FIG. 10. A body weight increase of five mice of each group loaded with a normal diet and a high fat diet (HFD) is observed. Loading with a high fat diet (HFD) causes an obvious body weight increase compared with loading with a normal diet.

2) FIG. 11 shows changes in body weight of mice loaded with a high fat diet (HFD) after they are administered with D-allulose.

After 4-week loading with a high fat diet (HFD) before D-allulose administration, no difference in body weight increase is observed between two groups.

From week 2 after D-allulose administration is started (week 6 after a high fat diet is started), a significant difference in body weight is observed between two groups.

In the D-allulose administered group, an increasing degree of body weight lowers significantly from week 2 after administration is started.

3) The results of the transition of fasting blood glucose levels are shown in FIG. 12.

Changes in body weight of mice loaded with a high fat diet (HFD) when they are administered with D-allulose are shown. From week 3 after D-allulose administration is started (week 6 after a high fat diet is started), a reduction in fasting blood glucose level is observed.

4) The results of the transition of a blood glucose level in the glucose loading test after 10 weeks are shown in FIG. 13.

Glucose was intraperitoneally administered and the blood glucose level after 0, 15, 30, 60, 90, and 120 minutes were measured. In the D-allulose administered group, the blood glucose levels after 90 and 120 minutes significantly decreases as compared with those of the control group.

5) As shown in FIG. 14, there is no significant change in food intake (right-side drawing) and water intake (the left side drawing) between two groups during the research term.

6) Investigation results on the weight and area of brown adipocytes (BAT) when D-allulose was administered to the mice loaded with a high fat diet (HFD) are shown in FIG. 15.

In the D-allulose administered group, an increase in the weight and area of brown adipocytes (BAT) are observed, showing results similar to those of Example 1.

According to the morphological investigation of brown adipocytes (BAT), similar to FIG. 3 of Example 1, the histological image of brown adipocytes (BAT) of mice loaded with a high fat diet (HFD) shows overall deposition of fat and advance of fatification as compared with the histological image of brown adipocytes (BAT) of mice taking a normal diet, while the histological image of brown adipocytes (BAT) of the group loaded with high fat diet (HFD) and 2% D-allulose-containing water was almost morphologically similar to that of the normal diet intake group and fat deposition observed in the group loaded with a high fat diet (HFD) was not observed.

(Adipose Tissue)

Adipose tissue based on the current thinking (Non-Patent Document 3) will next be described referring to FIG. 16.

Beige adipocytes or beige adipocytes were isolated as third adipocytes in 2012 by Dr. Bruce Spiegelman's research team of the Dana-Farber Cancer Institute at Harvard Medical School.

Adipocytes include white adipocytes which accumulate fat and brown adipocytes having a function of burning fat and generating heat. In brown adipocytes, a protein called "uncoupling protein" (uncoupling protein 1: UCP-1) is expressed much and this UCP-1 serves to generate heat, burn fat, and convert it into energy. UCP-1 expression in beige adipocytes is very low as in white adipocytes but UCP-1 is highly expressed by the stimulation such as cold. When stimulated, these adipocytes, similar to brown adipocytes, start thermogenesis and white adipocytes have brown adipocyte-like properties. Brown adipocytes and beige adipocytes contribute to body temperature maintenance in a cold environment as special adipocytes producing heat in response to cold exposure. The thermogenesis and energy consumption activities of these adipocytes are expected to be useful not only as body temperature regulating ability but also for prevention of obesity or metabolic diseases. Brown adipocytes and beige adipocytes express UCP-1 and have thermogenesis ability in common, but it has been understood that they are different from each other in the origin of cells or function control mechanism. Classical brown adipocytes have been developed in small rodents, particularly hibernators, and exist as a brown adipocyte cluster between the scapula, in the axilla, or around the kidney. The differentiation and tissue formation of brown adipocytes are completed in the fetal stage, while differentiation of beige adipocytes is induced in response to stimulation such as exposure to a cold environment and they disappear without stimulation. This inducibility and flexibility may be the largest characteristics as compared with "existing type" brown adipocytes or white adipocytes which continue existing from the time of their appearance.

From the standpoint of functional characteristics, different from white adipocytes which store excess energy as neutral fat, brown adipocytes and beige adipocytes perform thermogenesis through UCP-1 which uncouples oxidative phosphorylation. In this point, beige adipocytes are similar to brown adipocytes.

In recent years, a research using positron diagnostic imaging (fluorodeoxyglucose-positron emission tomography: FDG-PET) has revealed that a certain amount of brown adipocytes (BAT) is present also in humans. BAT in humans is present between the scapula, around the kidney, at the supraclavicular fossa, under the axilla, in the paravertebral region, or the like. Recent research has suggested that BAT possessed by adults is composed mainly of beige adipocytes. This is supported also by the fact that the BAT activity of adults becomes lowest in summer and highest in winter, that is, it has inducibility and flexibility. A negative correlation is found between the amount of change in BAT activity and the amount of change in body fat. These results have revealed that human BAT (beige adipocytes) becomes an effective stimulation target for reducing obesity.

7) The investigation results of the expression of UCP-1 mRNA in beige adipocytes and brown adipocytes in high fat diet (HFD)-loaded mice after administration of D-allulose thereto are shown in FIG. 17.

On the left-side drawing, the UCP-1 expression is significantly increased in beige adipocytes by the administration of D-allulose. This suggests that D-allulose causes the differentiation induction of beige adipocytes.

On the right-side drawing, the UCP-1 expression is increased even in the classical brown adipose tissue.

The administration of D-allulose has a possibility of contributing to a weight loss by inducing beige adipocytes and activating brown adipocytes.

8) The investigation results of the expression of UCP-1 protein in beige adipocytes and brown adipocytes in high fat diet (HFD)-loaded mice after administration of D-allulose thereto are shown in FIG. 18.

On the left-side drawing, the expression of UCP-1 protein is significantly increased in beige adipocytes by the administration of D-allulose. This suggests that D-allulose causes the differentiation induction of beige adipocytes.

On the right-side drawing, the expression of UCP-1 protein is increased even in the classical brown adipose tissue.

The administration of D-allulose has a possibility of contributing a weight loss by inducing beige adipocytes and activating brown adipocytes.

9) With regard to the details of the induction of beige adipocytes and the activation of brown adipocytes caused by D-allulose administration, expression of UCP-1 and Prdm16 which are genes involved in thermogenesis, Pgcl-α and Tfam which are genes reflecting the mitochondrial function of organelle involved in thermogenesis, and PPARγ which is a gene related to the differentiation of fat are investigated and the results are shown in FIG. 19.

The drawing on the left side shows that according to the investigation of beige adipocytes, expression of UCP-1, Prdm16, Pgcl-α, Tfam, and PPARγ is increased, suggesting that beige adipocytes have been induced strongly.

The drawing on the right side shows increase of UCP-1, Prdm16, and Tfam expression in brown adipocytes. They are presumed to participate in the activation of brown adipocytes.

10) FIG. 20 is a drawing for describing two protocols for inducing beige adipocytes, that is, BAT-protocol and WAT-protocol used in an experiment using cells (a cell line derived from a single clone from BAT of the adult supraclavicular fossa is established and used as a research model of the differentiation induction into beige adipocytes).

FIG. 21 is a drawing for describing a protocol including two protocols for inducing beige adipocytes, that is, BAT-protocol and WAT-protocol and further including addition of D-allulose in an experiment using cells.

FIG. 22 shows by fat staining that addition of D-allulose to the differentiation inducing protocol, induction into beige adipocytes is promoted.

The addition of D-allulose (right) promotes oil-red-O (fat staining).

In FIG. 23 shows investigation of expression of various markers for evaluating beige adipocytes induced by a differentiation inducing protocol. The WAT-protocol has a stronger influence on the induction of browning marker genes (UCP-1, Pgc-1α, cox8b). When the WAT-protocol is used, D-allulose enhances the expression of Prdm16, Pgc-1α, and PPARγ.

This suggests that in both differentiation protocols, D-allulose enhances expression of PPARγ and D-allulose promotes adipogenesis.

This means that in the D-allulose administered group, expression of all the markers is significantly increased and a beige adipocyte induction process is significantly promoted.

In FIG. 24, the expression of various markers is investigated as the evaluation of beige adipocytes induced by the protocol. UCP-1 and PPARγ are investigated in the presence or absence of D-allulose. Expression of UCP-1 and PPARγ are increased in the presence of D-allulose, showing that the induction of beige adipocytes has been promoted.

Compared with the BAT-protocol, the WAT-protocol has a stronger influence on the induction of UCP-1 protein expression. When the WAT-protocol is used, D-allulose slightly enhances the expression of UCP-1 protein.

3. Conclusive Discussion.

A body weight reduction due to D-allulose administration is observed. This body weight reduction effect is presumed to be result from the differentiation induction of beige adipocytes and the activation of brown adipocytes.

INDUSTRIAL APPLICABILITY

Intake of the brown adipocyte activating agent of the present application containing D-allulose activates brown adipocytes or beige adipocytes and promotes systemic energy consumption, which is expected to decrease the amount of fat and eventually eliminate obesity. In fact, intake of D-allulose (15 g a day by humans caused a weight reduction with a significant difference after 3 months. This has suggested that also in humans, the activating agent contributes to proliferation of brown adipose tissue and acquisition of a "constitution easy to lose weight". In general, metabolism decreases and the body feels chills with aging, but intake of D-allulose is expected to increase energy metabolism (thermogenesis) and thereby prevent and improve chills in the body. Further, the brown adipocyte activating action of D-allulose is expected to cause differentiation induction of brown-like adipocytes (beige adipocytes) into white adipose tissue.

The invention claimed is:
1. A method of activating brown adipocytes and beige adipocytes in an adult mammal, comprising:
administering D-allulose or a composition containing D-allulose as an active ingredient to the adult mammal for at least two weeks in need of activating brown adipocytes and beige adipocytes thereof, wherein the term "activating" means increasing a weight and area of brown adipocytes and beige adipocytes in somatic cells and activating a function of the brown adipocytes and beige adipocytes.

2. The method according to claim 1, wherein the composition is a food or beverage composition.

3. The method according to claim 1, wherein the D-allulose or a composition containing D-allulose is administered to the adult mammal in need of the activation of brown adipocytes and beige adipocytes via a UCP1 independent mechanism.

4. The method according to claim 1, wherein the function activating action is UCP-1 expression promoting action.

5. The method according to claim 1, wherein the function activating action is action of promoting differentiation induction of the beige adipocytes in white adipose tissues.

6. A method of activating brown adipocytes and beige adipocytes to promote energy consumption of somatic cells in an adult mammal, comprising:

administering D-allulose or a composition containing D-allulose as an active ingredient to the adult mammal for at least two weeks in need of activating brown adipocytes and beige adipocytes thereof to promote energy consumption of somatic cells, wherein the term "activating" means increasing a weight and area of brown adipocytes and beige adipocytes in somatic cells and activating an energy consumption promoting function of the brown adipocytes and beige adipocytes.

7. A method of activating brown adipocytes and beige adipocytes to enhance UCP-1 expression of somatic cells and promoting differentiation induction of the beige adipocytes in white adipose tissues in adult mammal, comprising:

administering D-allulose or a composition containing D-allulose as an active ingredient to the adult mammal for at least two weeks in need of activating brown adipocytes and beige adipocytes to enhance UCP-1 expression of somatic cells and promoting differentiation induction of the beige adipocytes in white adipose tissues.

* * * * *